(12) United States Patent
Becking et al.

(10) Patent No.: US 11,707,371 B2
(45) Date of Patent: *Jul. 25, 2023

(54) BRAID IMPLANT DELIVERY SYSTEMS

(71) Applicant: Covidien LP, Mansfield, MA (US)

(72) Inventors: Frank P. Becking, Santa Clara, CA (US); Maria G. Aboytes, Palo Alto, CA (US); Arturo S. Rosqueta, San Jose, CA (US)

(73) Assignee: COVIDIEN LP, Mansfield, MA (US)

( * ) Notice: Subject to any disclaimer, the term of this patent is extended or adjusted under 35 U.S.C. 154(b) by 696 days.

This patent is subject to a terminal disclaimer.

(21) Appl. No.: 16/806,766

(22) Filed: Mar. 2, 2020

(65) Prior Publication Data

US 2020/0197203 A1 Jun. 25, 2020

Related U.S. Application Data

(60) Continuation of application No. 15/598,357, filed on May 18, 2017, now Pat. No. 10,610,389, which is a
(Continued)

(51) Int. Cl.
| | | |
|---|---|---|
| *A61F 2/95* | (2013.01) | |
| *A61F 2/97* | (2013.01) | |
| *A61F 2/966* | (2013.01) | |
| *A61F 2/24* | (2006.01) | |
| *A61F 2/90* | (2013.01) | |

(Continued)

(52) U.S. Cl.
CPC .............. *A61F 2/95* (2013.01); *A61F 2/9662* (2020.05); *A61F 2/97* (2013.01); *A61F 2/243* (2013.01); *A61F 2/2427* (2013.01); *A61F 2/90* (2013.01); *A61F 2/958* (2013.01);
(Continued)

(58) Field of Classification Search
CPC .... A61F 2/95; A61F 2/243; A61F 2/90; A61F 2/958; A61F 2002/9505; A61F 2/97
See application file for complete search history.

(56) References Cited

U.S. PATENT DOCUMENTS

| | | | |
|---|---|---|---|
| 3,108,593 A | 10/1963 | Glassman | |
| 4,321,711 A | 3/1982 | Mano | |

(Continued)

FOREIGN PATENT DOCUMENTS

| | | | |
|---|---|---|---|
| CA | 2607529 A1 | 4/2008 | |
| CN | 101472537 A | 7/2009 | |

(Continued)

OTHER PUBLICATIONS

Benndor, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.
(Continued)

*Primary Examiner* — Diane D Yabut
*Assistant Examiner* — Christina C Lauer
(74) *Attorney, Agent, or Firm* — Fortem IP LLP

(57) ABSTRACT

Embolic implants delivery systems and methods of manufacture and delivery are disclosed. The devices can be used for aneurysm and/or fistula treatment. The designs offer low profile compressibility for delivery to neurovasculature, while maintaining advantageous delivery and implant detachment control features.

20 Claims, 9 Drawing Sheets

Related U.S. Application Data division of application No. 12/465,475, filed on May 13, 2009, now Pat. No. 9,675,482.

(60) Provisional application No. 61/083,959, filed on Jul. 28, 2008, provisional application No. 61/052,756, filed on May 13, 2008.

(51) Int. Cl.
  *A61F 2/958* (2013.01)
  *A61F 2/962* (2013.01)

(52) U.S. Cl.
  CPC ............... *A61F 2002/9505* (2013.01); *A61F 2002/9511* (2013.01); *A61F 2002/9623* (2020.05)

(56) References Cited

U.S. PATENT DOCUMENTS

| | | |
|---|---|---|
| 4,425,908 A | 1/1984 | Simon |
| 4,503,569 A | 3/1985 | Dotter |
| 4,512,338 A | 4/1985 | Balko et al. |
| 4,538,622 A | 9/1985 | Samson et al. |
| 4,580,568 A | 4/1986 | Gianturco |
| 4,619,246 A | 10/1986 | Molgaard-Nielsen et al. |
| 4,655,771 A | 4/1987 | Wallsten |
| 4,733,665 A | 3/1988 | Palmaz |
| 4,768,507 A | 9/1988 | Fischell et al. |
| 4,776,337 A | 10/1988 | Palmaz |
| 4,921,484 A | 5/1990 | Hillstead |
| 4,954,126 A | 9/1990 | Wallsten |
| 4,998,539 A | 3/1991 | Delsanti |
| 5,011,488 A | 4/1991 | Ginsburg |
| 5,026,377 A | 6/1991 | Burton et al. |
| 5,035,706 A | 7/1991 | Giantureo et al. |
| 5,061,275 A | 10/1991 | Wallsten et al. |
| 5,064,435 A | 11/1991 | Porter |
| 5,104,404 A | 4/1992 | Wolff |
| 5,108,416 A | 4/1992 | Ryan et al. |
| 5,122,136 A | 6/1992 | Guglielml et al. |
| 5,147,370 A | 9/1992 | Mcnamara et al. |
| 5,158,548 A | 10/1992 | Lau et al. |
| 5,160,341 A | 11/1992 | Brenneman et al. |
| 5,180,368 A | 1/1993 | Garrison |
| 5,192,297 A | 3/1993 | Hull |
| 5,201,757 A * | 4/1993 | Heyn .................. A61F 2/97 606/198 |
| 5,209,731 A | 5/1993 | Sterman et al. |
| 5,222,971 A | 6/1993 | Willard et al. |
| 5,242,399 A | 9/1993 | Lau et al. |
| 5,246,420 A | 9/1993 | Kraus et al. |
| 5,246,445 A | 9/1993 | Yachia et al. |
| 5,250,071 A | 10/1993 | Palermo |
| 5,284,488 A | 2/1994 | Sideris |
| 5,326,350 A | 7/1994 | Li |
| 5,334,210 A | 8/1994 | Gianturco |
| 5,344,426 A | 9/1994 | Lau et al. |
| 5,354,295 A | 10/1994 | Guglielmi et al. |
| 5,360,443 A | 11/1994 | Barone et al. |
| 5,378,239 A | 1/1995 | Termin et al. |
| 5,382,259 A | 1/1995 | Phelps et al. |
| 5,401,257 A | 3/1995 | Chevalier, Jr. et al. |
| 5,405,379 A | 4/1995 | Lane |
| 5,405,380 A | 4/1995 | Gianotti et al. |
| 5,415,637 A | 5/1995 | Khosravi |
| 5,417,708 A | 5/1995 | Hall et al. |
| 5,421,826 A | 6/1995 | Crocker et al. |
| 5,423,849 A | 6/1995 | Engelson et al. |
| 5,425,984 A | 6/1995 | Kennedy et al. |
| 5,445,646 A | 8/1995 | Euteneuer et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler et al. |
| 5,489,295 A | 2/1996 | Piplani et al. |
| 5,499,981 A | 3/1996 | Kordis |
| 5,503,636 A | 4/1996 | Schmitt et al. |
| 5,507,768 A | 4/1996 | Lau et al. |
| 5,522,822 A | 6/1996 | Phelps et al. |
| 5,527,338 A | 6/1996 | Purdy |
| 5,534,007 A | 7/1996 | St. Germain et al. |
| 5,545,208 A | 8/1996 | Wolff et al. |
| 5,545,209 A | 8/1996 | Roberts et al. |
| 5,549,635 A | 8/1996 | Solar |
| 5,562,641 A | 10/1996 | Flomenblit et al. |
| 5,562,728 A | 10/1996 | Lazarus et al. |
| 5,591,225 A | 1/1997 | Okuda |
| 5,599,291 A | 2/1997 | Balbierz et al. |
| 5,607,466 A | 3/1997 | Imbert et al. |
| 5,609,625 A | 3/1997 | Piplani et al. |
| 5,624,461 A | 4/1997 | Mariant |
| 5,626,602 A | 5/1997 | Gianotti et al. |
| 5,628,783 A | 5/1997 | Quiachon et al. |
| 5,632,772 A | 5/1997 | Alcime et al. |
| 5,634,942 A | 6/1997 | Chevillon et al. |
| 5,636,641 A | 6/1997 | Fariabi |
| 5,643,278 A | 7/1997 | Wijay |
| 5,645,558 A | 7/1997 | Horton |
| 5,662,703 A | 9/1997 | Yurek et al. |
| 5,667,522 A | 9/1997 | Flomenblit et al. |
| 5,669,931 A | 9/1997 | Kupiecki et al. |
| 5,674,276 A | 10/1997 | Andersen et al. |
| 5,683,451 A | 11/1997 | Lenker et al. |
| 5,690,120 A | 11/1997 | Jacobsen et al. |
| 5,690,643 A | 11/1997 | Wijay |
| 5,690,644 A | 11/1997 | Yurek et al. |
| 5,690,671 A | 11/1997 | McGurk et al. |
| 5,695,499 A | 12/1997 | Helgerson et al. |
| 5,700,269 A | 12/1997 | Pinchuk et al. |
| 5,702,418 A | 12/1997 | Ravenscroft |
| 5,702,419 A | 12/1997 | Berry et al. |
| 5,709,702 A | 1/1998 | Cogita |
| 5,709,703 A | 1/1998 | Lukic et al. |
| 5,713,907 A | 2/1998 | Wholey et al. |
| 5,725,552 A | 3/1998 | Kotula et al. |
| 5,725,570 A | 3/1998 | Heath |
| 5,725,571 A | 3/1998 | Imbert et al. |
| 5,728,906 A | 3/1998 | Eguchi et al. |
| 5,733,294 A | 3/1998 | Forber et al. |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid |
| 5,749,883 A | 5/1998 | Halpern |
| 5,749,891 A | 5/1998 | Ken et al. |
| 5,749,895 A | 5/1998 | Sawyer et al. |
| 5,749,919 A | 5/1998 | Blanc |
| 5,749,920 A | 5/1998 | Quiachon et al. |
| 5,766,151 A | 6/1998 | Valley et al. |
| 5,769,884 A | 6/1998 | Solovay |
| 5,769,885 A | 6/1998 | Quiachon et al. |
| 5,776,099 A | 7/1998 | Tremulis |
| 5,776,140 A | 7/1998 | Cottone |
| 5,776,141 A | 7/1998 | Klein et al. |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Piplani et al. |
| 5,807,398 A | 9/1998 | Shaknovich |
| 5,810,837 A | 9/1998 | Hofmann et al. |
| 5,814,062 A | 9/1998 | Sepetka et al. |
| 5,817,102 A | 10/1998 | Johnson et al. |
| 5,823,198 A | 10/1998 | Jones et al. |
| 5,824,039 A | 10/1998 | Piplani et al. |
| 5,824,041 A | 10/1998 | Lenker et al. |
| 5,824,044 A | 10/1998 | Quiachon et al. |
| 5,824,058 A | 10/1998 | Ravenscroft et al. |
| 5,830,230 A | 11/1998 | Berryman et al. |
| 5,833,632 A | 11/1998 | Jacobsen et al. |
| 5,836,868 A | 11/1998 | Ressemann et al. |
| 5,846,261 A | 12/1998 | Kotula et al. |
| 5,853,422 A | 12/1998 | Huebsch et al. |
| 5,855,578 A | 1/1999 | Guglielmi et al. |

(56) References Cited

U.S. PATENT DOCUMENTS

| | | |
|---|---|---|
| 5,868,754 A | 2/1999 | Levine et al. |
| 5,873,907 A | 2/1999 | Frantzen |
| 5,879,366 A | 3/1999 | Shaw et al. |
| 5,888,201 A | 3/1999 | Stinson et al. |
| 5,902,266 A | 5/1999 | Leone et al. |
| 5,906,640 A | 5/1999 | Penn et al. |
| 5,908,435 A | 6/1999 | Samuels |
| 5,911,717 A | 6/1999 | Jacobsen et al. |
| 5,911,731 A | 6/1999 | Pham et al. |
| 5,916,194 A | 6/1999 | Jacobsen et al. |
| 5,916,235 A | 6/1999 | Guglielmi |
| 5,919,204 A | 7/1999 | Lukic et al. |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,726 A | 8/1999 | Blaeser et al. |
| 5,944,738 A | 8/1999 | Amplatz et al. |
| 5,951,599 A | 9/1999 | Mccrory |
| 5,957,948 A | 9/1999 | Mariant |
| 5,957,973 A | 9/1999 | Quiachon et al. |
| 5,957,974 A | 9/1999 | Thompson et al. |
| 5,964,797 A | 10/1999 | Ho |
| 5,972,015 A | 10/1999 | Scribner et al. |
| 5,976,162 A | 11/1999 | Doan et al. |
| 5,976,169 A | 11/1999 | Imran |
| 5,980,530 A | 11/1999 | Willard et al. |
| 5,980,533 A | 11/1999 | Holman |
| 5,980,554 A | 11/1999 | Lenker et al. |
| 5,984,929 A | 11/1999 | Bashiri et al. |
| 6,001,092 A | 12/1999 | Mirigian et al. |
| 6,010,517 A | 1/2000 | Baccaro |
| 6,014,919 A | 1/2000 | Jacobsen et al. |
| 6,015,432 A | 1/2000 | Rakos et al. |
| 6,017,319 A | 1/2000 | Jacobsen et al. |
| 6,019,778 A | 2/2000 | Wilson et al. |
| 6,019,786 A | 2/2000 | Thompson |
| 6,022,369 A | 2/2000 | Jacobsen et al. |
| 6,022,374 A | 2/2000 | Imran |
| 6,024,754 A | 2/2000 | Engelson |
| 6,024,756 A | 2/2000 | Huebsch et al. |
| 6,024,763 A | 2/2000 | Lenker et al. |
| 6,027,516 A | 2/2000 | Kolobow et al. |
| 6,033,423 A | 3/2000 | Ken et al. |
| 6,036,720 A | 3/2000 | Abrams et al. |
| 6,039,758 A | 3/2000 | Quiachon et al. |
| 6,042,589 A | 3/2000 | Marianne |
| 6,051,021 A | 4/2000 | Frid |
| 6,056,993 A | 5/2000 | Leidner et al. |
| 6,059,813 A | 5/2000 | Vrba et al. |
| 6,063,070 A | 5/2000 | Eder |
| 6,063,104 A | 5/2000 | Villar et al. |
| 6,063,111 A | 5/2000 | Hieshima et al. |
| 6,068,634 A | 5/2000 | Lorentzen Cornelius et al. |
| 6,074,407 A | 6/2000 | Levine et al. |
| 6,077,295 A | 6/2000 | Limon et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,096,052 A | 8/2000 | Callister et al. |
| 6,096,073 A | 8/2000 | Webster et al. |
| 6,099,526 A | 8/2000 | Whayne et al. |
| 6,102,942 A | 8/2000 | Ahari |
| 6,106,530 A | 8/2000 | Harada |
| 6,110,191 A | 8/2000 | Dehdashtian et al. |
| 6,113,607 A | 9/2000 | Lau et al. |
| 6,123,712 A | 9/2000 | Di Caprio et al. |
| 6,123,715 A | 9/2000 | Amplatz |
| 6,126,685 A | 10/2000 | Lenker et al. |
| 6,132,459 A | 10/2000 | Piplani et al. |
| 6,139,543 A | 10/2000 | Esch et al. |
| 6,139,564 A | 10/2000 | Teoh |
| 6,146,415 A | 11/2000 | Fitz |
| 6,149,680 A | 11/2000 | Shelso et al. |
| 6,152,144 A | 11/2000 | Lesh et al. |
| 6,159,531 A | 12/2000 | Dang et al. |
| 6,165,178 A | 12/2000 | Bashiri et al. |
| 6,165,193 A | 12/2000 | Greene et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,410 B1 | 2/2001 | Jacobsen et al. |
| 6,183,495 B1 | 2/2001 | Lenker et al. |
| 6,190,402 B1 | 2/2001 | Horton et al. |
| 6,193,708 B1 | 2/2001 | Ken et al. |
| 6,197,046 B1 | 3/2001 | Piplani et al. |
| 6,206,868 B1 | 3/2001 | Parodi |
| 6,210,400 B1 | 4/2001 | Hebert et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,042 B1 | 4/2001 | Jacobsen et al. |
| 6,221,086 B1 | 4/2001 | Forber |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,597 B1 | 5/2001 | Deem et al. |
| 6,235,050 B1 | 5/2001 | Quiachon et al. |
| 6,238,403 B1 | 5/2001 | Greene et al. |
| 6,241,758 B1 | 6/2001 | Cox |
| 6,241,759 B1 | 6/2001 | Piplani et al. |
| 6,245,103 B1 | 6/2001 | Stinson |
| 6,251,132 B1 | 6/2001 | Ravenscroft et al. |
| 6,260,458 B1 | 7/2001 | Jacobsen et al. |
| 6,261,305 B1 | 7/2001 | Marotta et al. |
| 6,270,523 B1 | 8/2001 | Herweck et al. |
| 6,280,412 B1 | 8/2001 | Pederson et al. |
| 6,280,465 B1 | 8/2001 | Cryer |
| 6,287,331 B1 | 9/2001 | Heath |
| 6,290,721 B1 | 9/2001 | Heath |
| 6,299,619 B1 | 10/2001 | Greene et al. |
| 6,302,810 B2 | 10/2001 | Yokota |
| 6,302,893 B1 | 10/2001 | Limon et al. |
| 6,306,141 B1 | 10/2001 | Jervis |
| 6,309,367 B1 | 10/2001 | Boock |
| 6,322,576 B1 | 11/2001 | Wallace et al. |
| 6,322,586 B1 | 11/2001 | Monroe et al. |
| 6,322,587 B1 | 11/2001 | Quiachon et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,348,063 B1 | 2/2002 | Yassour et al. |
| 6,350,199 B1 | 2/2002 | Williams et al. |
| 6,350,270 B1 | 2/2002 | Roue |
| 6,350,278 B1 | 2/2002 | Lenker et al. |
| 6,355,061 B1 | 3/2002 | Quiachon et al. |
| 6,361,558 B1 | 3/2002 | Hieshima et al. |
| 6,364,895 B1 | 4/2002 | Greenhalgh |
| 6,368,339 B1 | 4/2002 | Amplatz |
| 6,368,344 B1 | 4/2002 | Fitz |
| 6,368,557 B1 | 4/2002 | Piplani et al. |
| 6,371,928 B1 | 4/2002 | Mcfann et al. |
| 6,371,980 B1 | 4/2002 | Rudakov et al. |
| 6,375,668 B1 | 4/2002 | Gifford et al. |
| 6,375,670 B1 | 4/2002 | Greenhalgh |
| 6,375,676 B1 | 4/2002 | Cox |
| 6,379,372 B1 | 4/2002 | Dehdashtian et al. |
| 6,379,618 B1 | 4/2002 | Piplani et al. |
| 6,380,457 B1 | 4/2002 | Yurek et al. |
| 6,383,174 B1 | 5/2002 | Eder |
| 6,387,118 B1 | 5/2002 | Hanson |
| 6,391,037 B1 | 5/2002 | Greenhalgh |
| 6,395,017 B1 | 5/2002 | Dwyer et al. |
| 6,395,022 B1 | 5/2002 | Piplani et al. |
| 6,398,802 B1 | 6/2002 | Yee |

(56) References Cited

U.S. PATENT DOCUMENTS

| | | |
|---|---|---|
| 6,409,683 B1 | 6/2002 | Fonseca et al. |
| 6,409,750 B1 | 6/2002 | Hyodoh et al. |
| 6,413,235 B1 | 7/2002 | Parodi |
| 6,416,536 B1 | 7/2002 | Yee |
| 6,428,489 B1 | 8/2002 | Jacobsen et al. |
| 6,428,558 B1 | 8/2002 | Jones et al. |
| 6,432,130 B1 | 8/2002 | Hanson |
| 6,440,088 B1 | 8/2002 | Jacobsen et al. |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,531 B1 | 9/2002 | Amplatz |
| 6,451,025 B1 | 9/2002 | Jervis |
| 6,451,050 B1 | 9/2002 | Rudakov et al. |
| 6,454,780 B1 | 9/2002 | Wallace |
| 6,454,999 B1 | 9/2002 | Farhangnia et al. |
| 6,468,266 B1 | 10/2002 | Bashiri et al. |
| 6,478,778 B1 | 11/2002 | Jacobsen et al. |
| 6,482,221 B1 | 11/2002 | Hebert et al. |
| 6,491,648 B1 | 12/2002 | Cornish et al. |
| 6,494,884 B2 | 12/2002 | Gifford et al. |
| 6,503,450 B1 | 1/2003 | Afzal et al. |
| 6,506,204 B2 | 1/2003 | Mazzocchi |
| 6,511,468 B1 | 1/2003 | Cragg et al. |
| 6,514,261 B1 | 2/2003 | Randall et al. |
| 6,520,983 B1 | 2/2003 | Colgan et al. |
| 6,524,299 B1 | 2/2003 | Tran et al. |
| 6,527,763 B2 | 3/2003 | Esch et al. |
| 6,530,934 B1 | 3/2003 | Jacobsen et al. |
| 6,533,811 B1 | 3/2003 | Ryan et al. |
| 6,540,778 B1 | 4/2003 | Piplani et al. |
| 6,544,278 B1 | 4/2003 | Vrba et al. |
| 6,547,779 B2 | 4/2003 | Levine et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,572,646 B1 | 6/2003 | Boylan et al. |
| 6,576,006 B2 | 6/2003 | Limon et al. |
| 6,579,302 B2 | 6/2003 | Duerig et al. |
| 6,579,303 B2 | 6/2003 | Amplatz |
| 6,582,460 B1 | 6/2003 | Cryer |
| 6,585,748 B1 | 7/2003 | Jeffree |
| 6,585,756 B1 | 7/2003 | Strecker |
| 6,589,236 B2 | 7/2003 | Wheelock et al. |
| 6,589,256 B2 | 7/2003 | Forber |
| 6,589,265 B1 | 7/2003 | Palmer et al. |
| 6,589,273 B1 | 7/2003 | Mcdermott |
| 6,591,472 B1 | 7/2003 | Noone et al. |
| 6,592,605 B2 | 7/2003 | Lenker et al. |
| 6,592,616 B1 | 7/2003 | Stack et al. |
| 6,599,308 B2 | 7/2003 | Amplatz |
| 6,602,261 B2 | 8/2003 | Greene, Jr. et al. |
| 6,602,280 B2 | 8/2003 | Chobotov |
| 6,605,101 B1 | 8/2003 | Schaefer et al. |
| 6,605,102 B1 | 8/2003 | Mazzocchi et al. |
| 6,605,110 B2 | 8/2003 | Harrison |
| 6,605,111 B2 | 8/2003 | Bose et al. |
| 6,607,539 B1 | 8/2003 | Hayashi et al. |
| 6,607,551 B1 | 8/2003 | Sullivan et al. |
| 6,613,074 B1 | 9/2003 | Mitelberg et al. |
| 6,613,075 B1 | 9/2003 | Healy et al. |
| 6,623,518 B2 | 9/2003 | Thompson et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin et al. |
| 6,652,555 B1 | 11/2003 | Vantassel et al. |
| 6,652,556 B1 | 11/2003 | Vantassel et al. |
| 6,656,212 B2 | 12/2003 | Ravenscroft et al. |
| 6,656,218 B1 | 12/2003 | Denardo et al. |
| 6,660,024 B1 | 12/2003 | Flaherty et al. |
| 6,663,666 B1 | 12/2003 | Quiachon et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,719 B2 | 12/2003 | Wallace et al. |
| 6,669,721 B1 | 12/2003 | Bose et al. |
| 6,673,089 B1 | 1/2004 | Yassour et al. |
| 6,673,100 B2 | 1/2004 | Diaz et al. |
| 6,676,696 B1 | 1/2004 | Marotta et al. |
| 6,679,893 B1 | 1/2004 | Tran |
| 6,682,505 B2 | 1/2004 | Bates et al. |
| 6,682,546 B2 | 1/2004 | Amplatz |
| 6,682,557 B1 | 1/2004 | Quiachon et al. |
| 6,685,735 B1 | 2/2004 | Ahari |
| 6,689,150 B1 | 2/2004 | Vantassel et al. |
| 6,689,162 B1 | 2/2004 | Thompson |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,709,454 B1 | 3/2004 | Cox et al. |
| 6,709,465 B2 | 3/2004 | Mitchell et al. |
| 6,712,834 B2 | 3/2004 | Yassour et al. |
| 6,712,835 B2 | 3/2004 | Mazzocchi et al. |
| 6,716,238 B2 | 4/2004 | Elliott |
| 6,723,112 B2 | 4/2004 | Ho et al. |
| 6,723,116 B2 | 4/2004 | Taheri |
| 6,726,700 B1 | 4/2004 | Levine |
| 6,730,108 B2 | 5/2004 | Van Tassel et al. |
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,746,468 B1 | 6/2004 | Sepetka et al. |
| 6,746,890 B2 | 6/2004 | Gupta et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,780,196 B2 | 8/2004 | Chin et al. |
| 6,792,979 B2 | 9/2004 | Konya et al. |
| 6,793,667 B2 | 9/2004 | Hebert et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,855,153 B2 | 2/2005 | Saadat |
| 6,855,154 B2 | 2/2005 | Abdel-Gawwad |
| 6,858,034 B1 | 2/2005 | Hijlkema et al. |
| RE38,711 E | 3/2005 | Igaki et al. |
| 6,860,893 B2 | 3/2005 | Wallace et al. |
| 6,860,898 B2 | 3/2005 | Stack et al. |
| 6,860,901 B1 | 3/2005 | Baker et al. |
| 6,866,677 B2 | 3/2005 | Douk et al. |
| 6,866,680 B2 | 3/2005 | Yassour et al. |
| 6,878,384 B2 | 4/2005 | Cruise et al. |
| 6,887,267 B2 | 5/2005 | Dworschak et al. |
| 6,890,337 B2 | 5/2005 | Feeser et al. |
| 6,905,503 B2 | 6/2005 | Gifford et al. |
| 6,936,055 B1 | 8/2005 | Ken et al. |
| 6,949,103 B2 | 9/2005 | Mazzocchi et al. |
| 6,949,113 B2 | 9/2005 | Van et al. |
| 6,953,472 B2 | 10/2005 | Palmer et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,976,991 B2 | 12/2005 | Hebert et al. |
| 6,979,341 B2 | 12/2005 | Scribner et al. |
| 6,989,019 B2 | 1/2006 | Mazzocchi et al. |
| 6,989,024 B2 | 1/2006 | Hebert et al. |
| 6,991,617 B2 | 1/2006 | Hektner et al. |
| 6,994,092 B2 | 2/2006 | Van Der Burg et al. |
| 6,994,717 B2 | 2/2006 | Konya et al. |
| 6,994,721 B2 | 2/2006 | Israel |
| 7,001,422 B2 | 2/2006 | Escamilla et al. |

(56) References Cited

U.S. PATENT DOCUMENTS

| | | |
|---|---|---|
| 7,004,964 B2 | 2/2006 | Thompson et al. |
| 7,011,671 B2 | 3/2006 | Welch |
| 7,011,675 B2 | 3/2006 | Hemerick et al. |
| 7,014,645 B2 | 3/2006 | Greene et al. |
| 7,018,401 B1 | 3/2006 | Hyodoh et al. |
| 7,029,487 B2 | 4/2006 | Greene, Jr. et al. |
| 7,029,949 B2 | 4/2006 | Farnworth et al. |
| 7,033,375 B2 | 4/2006 | Mazzocchi et al. |
| 7,037,330 B1 | 5/2006 | Rivelli, Jr. et al. |
| 7,048,752 B2 | 5/2006 | Mazzocchi et al. |
| 7,063,679 B2 | 6/2006 | Maguire et al. |
| 7,066,951 B2 | 6/2006 | Chobotov |
| 7,069,835 B2 | 7/2006 | Nishri et al. |
| 7,070,607 B2 | 7/2006 | Murayama et al. |
| 7,070,609 B2 | 7/2006 | West |
| 7,074,236 B2 | 7/2006 | Rabkin et al. |
| 7,083,632 B2 | 8/2006 | Avellanet et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,125,419 B2 | 10/2006 | Sequin et al. |
| 7,128,073 B1 | 10/2006 | Van Der Burg et al. |
| 7,128,736 B1 | 10/2006 | Abrams et al. |
| 7,137,990 B2 | 11/2006 | Hebert et al. |
| 7,153,323 B1 | 12/2006 | Teoh et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,169,177 B2 | 1/2007 | Obara |
| 7,172,617 B2 | 2/2007 | Colgan et al. |
| 7,195,636 B2 | 3/2007 | Avellanet et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | Mccullagh et al. |
| 7,229,461 B2 | 6/2007 | Chin et al. |
| 7,232,461 B2 | 6/2007 | Ramer |
| 7,235,096 B1 | 6/2007 | Van Tassel et al. |
| 7,244,267 B2 | 7/2007 | Huter et al. |
| 7,261,720 B2 | 8/2007 | Stevens et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,303,571 B2 | 12/2007 | Makower et al. |
| 7,306,622 B2 | 12/2007 | Jones et al. |
| 7,306,624 B2 | 12/2007 | Yodfat et al. |
| 7,309,351 B2 | 12/2007 | Escamilla et al. |
| 7,311,031 B2 | 12/2007 | Mccullagh et al. |
| 7,320,702 B2 | 1/2008 | Hammersmark et al. |
| 7,326,225 B2 | 2/2008 | Ferrera et al. |
| 7,331,973 B2 | 2/2008 | Gesswein et al. |
| 7,331,976 B2 | 2/2008 | Mcguckin, Jr. et al. |
| 7,331,980 B2 | 2/2008 | Dubrul et al. |
| 7,331,985 B2 | 2/2008 | Thompson et al. |
| 7,338,518 B2 | 3/2008 | Chobotov |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,468,070 B2 | 12/2008 | Henry et al. |
| 7,470,282 B2 | 12/2008 | Shelso |
| 7,473,271 B2 | 1/2009 | Gunderson |
| 7,481,821 B2 | 1/2009 | Fogarty et al. |
| 7,485,088 B2 | 2/2009 | Murphy et al. |
| 7,491,214 B2 | 2/2009 | Greene et al. |
| 7,491,224 B2 | 2/2009 | Cox et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,575,590 B2 | 8/2009 | Watson |
| 7,578,826 B2 | 8/2009 | Gandhi et al. |
| 7,597,704 B2 | 10/2009 | Frazier et al. |
| 7,601,160 B2 | 10/2009 | Richter |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,708,754 B2 | 5/2010 | Balgobin et al. |
| 7,727,189 B2 | 6/2010 | Vantassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,785,361 B2 | 8/2010 | Nikolchev et al. |
| 7,828,815 B2 | 11/2010 | Mazzocchi et al. |
| 7,828,816 B2 | 11/2010 | Mazzocchi et al. |
| 7,862,602 B2 | 1/2011 | Licata et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,976,527 B2 | 7/2011 | Cragg et al. |
| RE42,625 E | 8/2011 | Guglielmi |
| 7,993,364 B2 | 8/2011 | Morsi |
| RE42,758 E | 9/2011 | Ken et al. |
| 8,012,210 B2 | 9/2011 | Lin et al. |
| 8,016,869 B2 | 9/2011 | Nikolchev |
| 8,016,872 B2 | 9/2011 | Parker |
| 8,043,326 B2 | 10/2011 | Hancock et al. |
| 8,062,379 B2 | 11/2011 | Morsi |
| 8,075,585 B2 | 12/2011 | Lee et al. |
| 8,114,154 B2 | 2/2012 | Righini et al. |
| 8,137,293 B2 | 3/2012 | Zhou et al. |
| 8,142,456 B2 | 3/2012 | Rosqueta et al. |
| 8,147,534 B2 | 4/2012 | Berez et al. |
| 8,192,480 B2 | 6/2012 | Tieu et al. |
| 8,202,280 B2 | 6/2012 | Richter |
| 8,206,431 B2 | 6/2012 | Seppala et al. |
| 8,211,160 B2 | 7/2012 | Garrison et al. |
| 8,221,445 B2 | 7/2012 | Van et al. |
| 8,236,042 B2 | 8/2012 | Berez et al. |
| 8,257,421 B2 | 9/2012 | Berez et al. |
| 8,261,648 B1 | 9/2012 | Marchand et al. |
| 8,267,985 B2 | 9/2012 | Garcia et al. |
| 8,273,101 B2 | 9/2012 | Garcia et al. |
| 8,298,257 B2 | 10/2012 | Sepetka et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,398,670 B2 | 3/2013 | Amplatz et al. |
| 8,425,541 B2 | 4/2013 | Masters et al. |
| 8,430,012 B1 | 4/2013 | Marchand et al. |
| 8,454,681 B2 | 6/2013 | Holman et al. |
| 8,470,013 B2 | 6/2013 | Duggal et al. |
| 8,597,320 B2 | 12/2013 | Sepetka et al. |
| 8,603,128 B2 | 12/2013 | Greene et al. |
| 8,715,317 B1 | 5/2014 | Janardhan et al. |
| 8,834,515 B2 | 9/2014 | Win et al. |
| 8,906,057 B2 | 12/2014 | Connor et al. |
| 8,974,512 B2 | 3/2015 | Aboytes et al. |
| 8,998,947 B2 | 4/2015 | Aboytes et al. |

(56) References Cited

U.S. PATENT DOCUMENTS

| | | | |
|---|---|---|---|
| 9,211,202 B2 | 12/2015 | Strother et al. | |
| 9,301,769 B2 | 4/2016 | Brady et al. | |
| 9,314,248 B2 | 4/2016 | Molaei | |
| 9,486,224 B2 | 11/2016 | Riina et al. | |
| 9,629,636 B2 | 4/2017 | Fogarty et al. | |
| 9,675,482 B2 * | 6/2017 | Becking | A61F 2/97 |
| 9,833,309 B2 | 12/2017 | Levi et al. | |
| 9,844,380 B2 | 12/2017 | Furey | |
| 9,907,684 B2 | 3/2018 | Connor et al. | |
| 9,962,146 B2 | 5/2018 | Hebert et al. | |
| 10,028,745 B2 | 7/2018 | Morsi | |
| 2001/0000797 A1 | 5/2001 | Mazzocchi | |
| 2001/0001835 A1 | 5/2001 | Greene et al. | |
| 2001/0007082 A1 | 7/2001 | Dusbabek et al. | |
| 2001/0012949 A1 | 8/2001 | Forber | |
| 2001/0012961 A1 | 8/2001 | Deem et al. | |
| 2001/0049547 A1 | 12/2001 | Moore | |
| 2001/0051822 A1 | 12/2001 | Stack et al. | |
| 2002/0013599 A1 | 1/2002 | Limon et al. | |
| 2002/0013618 A1 | 1/2002 | Marotta et al. | |
| 2002/0026210 A1 | 2/2002 | Abdel-Gawwad | |
| 2002/0042628 A1 | 4/2002 | Chin et al. | |
| 2002/0062091 A1 | 5/2002 | Jacobsen et al. | |
| 2002/0062145 A1 | 5/2002 | Rudakov et al. | |
| 2002/0078808 A1 | 6/2002 | Jacobsen et al. | |
| 2002/0087119 A1 | 7/2002 | Parodi | |
| 2002/0099405 A1 | 7/2002 | Yurek et al. | |
| 2002/0111647 A1 | 8/2002 | Khairkhahan et al. | |
| 2002/0119177 A1 | 8/2002 | Bowman et al. | |
| 2002/0120323 A1 | 8/2002 | Thompson et al. | |
| 2002/0143384 A1 | 10/2002 | Ozasa | |
| 2002/0147462 A1 | 10/2002 | Mair et al. | |
| 2002/0165572 A1 | 11/2002 | Saadat | |
| 2002/0169473 A1 | 11/2002 | Sepetka et al. | |
| 2002/0188341 A1 | 12/2002 | Elliott | |
| 2002/0193812 A1 | 12/2002 | Patel et al. | |
| 2002/0193813 A1 | 12/2002 | Helkowski et al. | |
| 2003/0004533 A1 | 1/2003 | Dieck et al. | |
| 2003/0004538 A1 | 1/2003 | Secrest et al. | |
| 2003/0004568 A1 | 1/2003 | Ken et al. | |
| 2003/0018294 A1 | 1/2003 | Cox | |
| 2003/0028209 A1 | 2/2003 | Teoh et al. | |
| 2003/0040772 A1 | 2/2003 | Hyodoh et al. | |
| 2003/0055440 A1 | 3/2003 | Jones et al. | |
| 2003/0057156 A1 | 3/2003 | Peterson et al. | |
| 2003/0069522 A1 | 4/2003 | Jacobsen et al. | |
| 2003/0093111 A1 | 5/2003 | Ken et al. | |
| 2003/0100945 A1 | 5/2003 | Yodfat et al. | |
| 2003/0109887 A1 | 6/2003 | Galdonik et al. | |
| 2003/0113478 A1 | 6/2003 | Dang et al. | |
| 2003/0114918 A1 | 6/2003 | Garrison et al. | |
| 2003/0135258 A1 | 7/2003 | Andreas et al. | |
| 2003/0149465 A1 | 8/2003 | Heidner et al. | |
| 2003/0149490 A1 | 8/2003 | Ashman | |
| 2003/0163155 A1 | 8/2003 | Haverkost et al. | |
| 2003/0163156 A1 | 8/2003 | Hebert et al. | |
| 2003/0171739 A1 | 9/2003 | Murphy et al. | |
| 2003/0171770 A1 | 9/2003 | Kusleika et al. | |
| 2003/0176884 A1 | 9/2003 | Berrada et al. | |
| 2003/0187473 A1 | 10/2003 | Berenstein et al. | |
| 2003/0195553 A1 | 10/2003 | Wallace et al. | |
| 2003/0199913 A1 | 10/2003 | Dubrul et al. | |
| 2003/0199919 A1 | 10/2003 | Palmer et al. | |
| 2003/0208256 A1 | 11/2003 | Dimatteo et al. | |
| 2003/0212419 A1 | 11/2003 | West | |
| 2003/0216693 A1 | 11/2003 | Mickley | |
| 2004/0015224 A1 * | 1/2004 | Armstrong | A61F 2/97 623/1.12 |
| 2004/0024416 A1 | 2/2004 | Yodfat et al. | |
| 2004/0034386 A1 | 2/2004 | Fulton et al. | |
| 2004/0044361 A1 | 3/2004 | Frazier et al. | |
| 2004/0044391 A1 | 3/2004 | Porter | |
| 2004/0044395 A1 | 3/2004 | Nelson | |
| 2004/0049204 A1 | 3/2004 | Harari et al. | |
| 2004/0049256 A1 | 3/2004 | Yee | |
| 2004/0059407 A1 | 3/2004 | Escamilla et al. | |
| 2004/0064093 A1 | 4/2004 | Hektner et al. | |
| 2004/0073300 A1 | 4/2004 | Chouinard et al. | |
| 2004/0078071 A1 | 4/2004 | Escamilla et al. | |
| 2004/0093010 A1 | 5/2004 | Gesswein et al. | |
| 2004/0093063 A1 | 5/2004 | Wright et al. | |
| 2004/0098027 A1 | 5/2004 | Teoh et al. | |
| 2004/0098028 A1 | 5/2004 | Martinez | |
| 2004/0098030 A1 | 5/2004 | Makower et al. | |
| 2004/0106945 A1 | 6/2004 | Thramann et al. | |
| 2004/0106977 A1 | 6/2004 | Sullivan et al. | |
| 2004/0111112 A1 | 6/2004 | Hoffmann | |
| 2004/0115164 A1 | 6/2004 | Pierce et al. | |
| 2004/0122467 A1 | 6/2004 | Vantassel et al. | |
| 2004/0122468 A1 | 6/2004 | Yodfat et al. | |
| 2004/0127912 A1 | 7/2004 | Rabkin et al. | |
| 2004/0138733 A1 | 7/2004 | Weber et al. | |
| 2004/0138758 A1 | 7/2004 | Kronengold et al. | |
| 2004/0143239 A1 | 7/2004 | Zhou et al. | |
| 2004/0143286 A1 | 7/2004 | Johnson et al. | |
| 2004/0153119 A1 | 8/2004 | Kusleika et al. | |
| 2004/0161451 A1 | 8/2004 | Pierce et al. | |
| 2004/0162606 A1 | 8/2004 | Thompson | |
| 2004/0172056 A1 | 9/2004 | Guterman et al. | |
| 2004/0172121 A1 | 9/2004 | Eidenschink et al. | |
| 2004/0181253 A1 | 9/2004 | Sepetka et al. | |
| 2004/0186551 A1 | 9/2004 | Kao et al. | |
| 2004/0186562 A1 | 9/2004 | Cox | |
| 2004/0193178 A1 | 9/2004 | Nikolchev | |
| 2004/0193179 A1 | 9/2004 | Nikolchev | |
| 2004/0193206 A1 | 9/2004 | Gerberding et al. | |
| 2004/0199243 A1 | 10/2004 | Yodfat | |
| 2004/0204749 A1 | 10/2004 | Gunderson | |
| 2004/0215229 A1 | 10/2004 | Coyle | |
| 2004/0215332 A1 | 10/2004 | Frid | |
| 2004/0220585 A1 * | 11/2004 | Nikolchev | A61B 17/1214 623/1.11 |
| 2004/0249408 A1 | 12/2004 | Murphy et al. | |
| 2004/0267346 A1 | 12/2004 | Shelso | |
| 2005/0010281 A1 | 1/2005 | Yodfat et al. | |
| 2005/0021077 A1 | 1/2005 | Chin et al. | |
| 2005/0033408 A1 | 2/2005 | Jones et al. | |
| 2005/0033409 A1 | 2/2005 | Burke et al. | |
| 2005/0049625 A1 | 3/2005 | Shaya et al. | |
| 2005/0049668 A1 | 3/2005 | Jones et al. | |
| 2005/0049670 A1 | 3/2005 | Jones et al. | |
| 2005/0060017 A1 | 3/2005 | Fischell et al. | |
| 2005/0090890 A1 | 4/2005 | Wu et al. | |
| 2005/0096728 A1 | 5/2005 | Ramer | |
| 2005/0096732 A1 | 5/2005 | Marotta et al. | |
| 2005/0107823 A1 | 5/2005 | Leone et al. | |
| 2005/0131443 A1 | 6/2005 | Abdel-Gawwad | |
| 2005/0131523 A1 | 6/2005 | Bashiri et al. | |
| 2005/0137680 A1 | 6/2005 | Ortiz et al. | |
| 2005/0209672 A1 | 9/2005 | George et al. | |
| 2005/0209674 A1 * | 9/2005 | Kutscher | A61M 25/1011 623/1.11 |
| 2005/0222580 A1 | 10/2005 | Gifford et al. | |
| 2005/0222605 A1 | 10/2005 | Greenhalgh et al. | |
| 2005/0228434 A1 | 10/2005 | Amplatz et al. | |
| 2005/0246010 A1 | 11/2005 | Alexander et al. | |
| 2005/0267510 A1 | 12/2005 | Razack | |
| 2005/0267511 A1 | 12/2005 | Marks et al. | |
| 2005/0267527 A1 | 12/2005 | Sandoval et al. | |
| 2005/0267568 A1 | 12/2005 | Berez et al. | |
| 2005/0273135 A1 | 12/2005 | Chanduszko et al. | |
| 2005/0277978 A1 | 12/2005 | Greenhalgh | |
| 2005/0278023 A1 | 12/2005 | Zwirkoski | |
| 2005/0283220 A1 | 12/2005 | Gobran et al. | |
| 2005/0283222 A1 | 12/2005 | Betelia et al. | |
| 2005/0288763 A1 | 12/2005 | Andreas et al. | |
| 2005/0288764 A1 | 12/2005 | Snow et al. | |
| 2005/0288766 A1 | 12/2005 | Plain et al. | |
| 2006/0025845 A1 | 2/2006 | Escamilla et al. | |
| 2006/0034883 A1 | 2/2006 | Dang et al. | |
| 2006/0036309 A1 | 2/2006 | Hebert et al. | |
| 2006/0052815 A1 | 3/2006 | Fitz et al. | |
| 2006/0052816 A1 | 3/2006 | Bates et al. | |
| 2006/0058865 A1 | 3/2006 | Case et al. | |

(56) References Cited

U.S. PATENT DOCUMENTS

| | | |
|---|---|---|
| 2006/0064151 A1 | 3/2006 | Guterman et al. |
| 2006/0074475 A1 | 4/2006 | Gumm |
| 2006/0089703 A1 | 4/2006 | Escamilla et al. |
| 2006/0095213 A1 | 5/2006 | Escamilla et al. |
| 2006/0106421 A1 | 5/2006 | Teoh |
| 2006/0111771 A1 | 5/2006 | Ton et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0116750 A1 | 6/2006 | Hebert et al. |
| 2006/0122548 A1 | 6/2006 | Abrams |
| 2006/0155323 A1 | 7/2006 | Porter et al. |
| 2006/0167494 A1 | 7/2006 | Suddaby |
| 2006/0184238 A1 | 8/2006 | Kaufmann et al. |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0217799 A1 | 9/2006 | Mailänder et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241686 A1 | 10/2006 | Ferrera et al. |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0271162 A1 | 11/2006 | Vito et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0003594 A1 | 1/2007 | Brady et al. |
| 2007/0005125 A1 | 1/2007 | Berenstein et al. |
| 2007/0010850 A1 | 1/2007 | Balgobin et al. |
| 2007/0014831 A1 | 1/2007 | Sung et al. |
| 2007/0016243 A1 | 1/2007 | Ramaiah et al. |
| 2007/0021816 A1 | 1/2007 | Rudin |
| 2007/0043419 A1 | 2/2007 | Nikolchev et al. |
| 2007/0050017 A1 | 3/2007 | Sims et al. |
| 2007/0055339 A1 | 3/2007 | George et al. |
| 2007/0073379 A1 | 3/2007 | Chang |
| 2007/0083226 A1 | 4/2007 | Buiser et al. |
| 2007/0088387 A1 | 4/2007 | Eskridge et al. |
| 2007/0093889 A1 | 4/2007 | Wu et al. |
| 2007/0100414 A1 | 5/2007 | Licata et al. |
| 2007/0100415 A1 | 5/2007 | Licata et al. |
| 2007/0100426 A1 | 5/2007 | Rudakov et al. |
| 2007/0106311 A1 | 5/2007 | Wallace et al. |
| 2007/0112415 A1 | 5/2007 | Bartlett |
| 2007/0119295 A1 | 5/2007 | Mccullagh et al. |
| 2007/0123969 A1 | 5/2007 | Gianotti |
| 2007/0135826 A1 | 6/2007 | Zaver et al. |
| 2007/0135907 A1 | 6/2007 | Wilson et al. |
| 2007/0150045 A1 | 6/2007 | Ferrera |
| 2007/0162104 A1 | 7/2007 | Frid |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0167980 A1 | 7/2007 | Figulla et al. |
| 2007/0173928 A1 | 7/2007 | Morsi |
| 2007/0175536 A1 | 8/2007 | Monetti et al. |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0191884 A1 | 8/2007 | Eskridge et al. |
| 2007/0191924 A1 | 8/2007 | Rudakov |
| 2007/0198059 A1 | 8/2007 | Patel et al. |
| 2007/0198075 A1 | 8/2007 | Levy |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0203567 A1 | 8/2007 | Levy |
| 2007/0208376 A1 | 9/2007 | Meng |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2007/0293935 A1 | 12/2007 | Olsen et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0003354 A1 | 1/2008 | Nolan |
| 2008/0009934 A1 | 1/2008 | Schneider et al. |
| 2008/0021535 A1 | 1/2008 | Leopold et al. |
| 2008/0033366 A1 | 2/2008 | Matson et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0081763 A1 | 4/2008 | Swetlin et al. |
| 2008/0082154 A1 | 4/2008 | Tseng et al. |
| 2008/0082176 A1 | 4/2008 | Slazas |
| 2008/0086196 A1 | 4/2008 | Truckai et al. |
| 2008/0097495 A1 | 4/2008 | Feller et al. |
| 2008/0109057 A1 | 5/2008 | Calabria et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0125852 A1 | 5/2008 | Garrison et al. |
| 2008/0132820 A1 | 6/2008 | Buckman et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0200945 A1 | 8/2008 | Amplatz et al. |
| 2008/0200979 A1 | 8/2008 | Dieck et al. |
| 2008/0208320 A1 | 8/2008 | Tan-malecki et al. |
| 2008/0219533 A1 | 9/2008 | Grigorescu |
| 2008/0221600 A1 | 9/2008 | Dieck et al. |
| 2008/0221666 A1 | 9/2008 | Licata et al. |
| 2008/0243226 A1 | 10/2008 | Fernandez et al. |
| 2008/0249562 A1 | 10/2008 | Cahill |
| 2008/0255654 A1 | 10/2008 | Hebert et al. |
| 2008/0262590 A1 | 10/2008 | Murray |
| 2008/0262598 A1 | 10/2008 | Elmaleh |
| 2008/0269774 A1 | 10/2008 | Garcia et al. |
| 2008/0281350 A1 | 11/2008 | Sepetka et al. |
| 2008/0300667 A1 | 12/2008 | Hebert et al. |
| 2008/0319533 A1 | 12/2008 | Lehe |
| 2009/0018637 A1 | 1/2009 | Paul et al. |
| 2009/0024202 A1 | 1/2009 | Dave et al. |
| 2009/0024205 A1 | 1/2009 | Hebert et al. |
| 2009/0024224 A1 | 1/2009 | Chen et al. |
| 2009/0025820 A1 | 1/2009 | Adams |
| 2009/0030496 A1 | 1/2009 | Kaufmann et al. |
| 2009/0030497 A1 | 1/2009 | Metcalf et al. |
| 2009/0043375 A1 | 2/2009 | Rudakov et al. |

(56) References Cited

U.S. PATENT DOCUMENTS

| | | |
|---|---|---|
| 2009/0056722 A1 | 3/2009 | Swann |
| 2009/0062899 A1 | 3/2009 | Dang et al. |
| 2009/0069806 A1 | 3/2009 | De et al. |
| 2009/0076540 A1 | 3/2009 | Marks et al. |
| 2009/0082803 A1 | 3/2009 | Adams et al. |
| 2009/0099647 A1 | 4/2009 | Glimsdale et al. |
| 2009/0105802 A1 | 4/2009 | Henry et al. |
| 2009/0105803 A1 | 4/2009 | Shelso |
| 2009/0112249 A1 | 4/2009 | Miles et al. |
| 2009/0112251 A1 | 4/2009 | Qian et al. |
| 2009/0118811 A1 | 5/2009 | Moloney |
| 2009/0125093 A1 | 5/2009 | Hansen |
| 2009/0125094 A1 | 5/2009 | Rust |
| 2009/0125119 A1 | 5/2009 | Obermiller et al. |
| 2009/0138065 A1 | 5/2009 | Zhang et al. |
| 2009/0143849 A1 | 6/2009 | Ozawa et al. |
| 2009/0143851 A1 | 6/2009 | Paul |
| 2009/0148492 A1 | 6/2009 | Dave et al. |
| 2009/0155367 A1 | 6/2009 | Neuwirth et al. |
| 2009/0163986 A1 | 6/2009 | Tieu et al. |
| 2009/0187214 A1 | 7/2009 | Amplatz et al. |
| 2009/0192536 A1 | 7/2009 | Berez et al. |
| 2009/0192587 A1 | 7/2009 | Frid |
| 2009/0198315 A1 | 8/2009 | Boudjemline |
| 2009/0198318 A1 | 8/2009 | Berez et al. |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0264978 A1 | 10/2009 | Dieck et al. |
| 2009/0270974 A1 | 10/2009 | Berez et al. |
| 2009/0275974 A1 | 11/2009 | Marchand et al. |
| 2009/0287241 A1 | 11/2009 | Berez et al. |
| 2009/0287288 A1 | 11/2009 | Berez et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0287297 A1 | 11/2009 | Cox |
| 2009/0292348 A1 | 11/2009 | Berez et al. |
| 2009/0297582 A1 | 12/2009 | Meyer et al. |
| 2009/0306702 A1 | 12/2009 | Miloslavski et al. |
| 2009/0318892 A1 | 12/2009 | Aboytes et al. |
| 2009/0318941 A1 | 12/2009 | Sepetka et al. |
| 2009/0318947 A1 | 12/2009 | Garcia et al. |
| 2009/0318948 A1 | 12/2009 | Davis et al. |
| 2009/0319017 A1 | 12/2009 | Berez et al. |
| 2009/0319023 A1 | 12/2009 | Hildebrand et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030200 A1 | 2/2010 | Strauss et al. |
| 2010/0030220 A1 | 2/2010 | Truckai et al. |
| 2010/0036390 A1 | 2/2010 | Gumm |
| 2010/0036410 A1 | 2/2010 | Krolik et al. |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0106178 A1 | 4/2010 | Obermiller et al. |
| 2010/0131002 A1 | 5/2010 | Connor et al. |
| 2010/0139465 A1 | 6/2010 | Christian et al. |
| 2010/0144895 A1 | 6/2010 | Porter |
| 2010/0152767 A1 | 6/2010 | Greenhalgh et al. |
| 2010/0174269 A1 | 7/2010 | Tompkins et al. |
| 2010/0185271 A1 | 7/2010 | Zhang |
| 2010/0222802 A1 | 9/2010 | Gillespie et al. |
| 2010/0228184 A1 | 9/2010 | Mavani et al. |
| 2010/0249830 A1 | 9/2010 | Nelson |
| 2010/0249894 A1 | 9/2010 | Oba et al. |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2010/0268204 A1 | 10/2010 | Tieu et al. |
| 2010/0268260 A1 | 10/2010 | Riina et al. |
| 2010/0274276 A1 | 10/2010 | Chow et al. |
| 2010/0298791 A1 | 11/2010 | Jones et al. |
| 2010/0305606 A1 | 12/2010 | Gandhi et al. |
| 2010/0312061 A1 | 12/2010 | Hess et al. |
| 2010/0312270 A1 | 12/2010 | Mcguckin et al. |
| 2010/0331948 A1 | 12/2010 | Turovskiy et al. |
| 2011/0022149 A1 | 1/2011 | Cox et al. |
| 2011/0046658 A1 | 2/2011 | Connor et al. |
| 2011/0054519 A1 | 3/2011 | Neuss |
| 2011/0077620 A1 | 3/2011 | Debeer |
| 2011/0082493 A1 | 4/2011 | Samson et al. |
| 2011/0106234 A1 | 5/2011 | Grandt |
| 2011/0125110 A1 | 5/2011 | Cotton |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0166588 A1 | 7/2011 | Connor et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0245862 A1 | 10/2011 | Dieck et al. |
| 2011/0251699 A1 | 10/2011 | Ladet |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0010644 A1 | 1/2012 | Sideris et al. |
| 2012/0022572 A1 | 1/2012 | Braun et al. |
| 2012/0041470 A1 | 2/2012 | Shrivastava et al. |
| 2012/0041472 A1 | 2/2012 | Tan et al. |
| 2012/0041474 A1 | 2/2012 | Eckhouse et al. |
| 2012/0065720 A1 | 3/2012 | Strauss et al. |
| 2012/0101510 A1 | 4/2012 | Lenker et al. |
| 2012/0101561 A1 | 4/2012 | Porter |
| 2012/0116350 A1 | 5/2012 | Strauss et al. |
| 2012/0143237 A1 | 6/2012 | Cam et al. |
| 2012/0143243 A1 | 6/2012 | Hill et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0221095 A1 | 8/2012 | Berez et al. |
| 2012/0226343 A1 | 9/2012 | Vo et al. |
| 2012/0239074 A1 | 9/2012 | Aboytes et al. |
| 2012/0245674 A1 | 9/2012 | Molaei et al. |
| 2012/0245675 A1 | 9/2012 | Molaei et al. |
| 2012/0277784 A1 | 11/2012 | Berez et al. |
| 2012/0283765 A1 | 11/2012 | Berez et al. |
| 2012/0283768 A1 | 11/2012 | Cox et al. |
| 2012/0283769 A1 | 11/2012 | Cruise et al. |
| 2012/0283815 A1 | 11/2012 | Berez et al. |
| 2012/0310269 A1 | 12/2012 | Fearnot et al. |
| 2012/0316598 A1 | 12/2012 | Becking et al. |
| 2012/0316632 A1 | 12/2012 | Gao |
| 2012/0323271 A1 | 12/2012 | Obermiller et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0116722 A1 | 5/2013 | Aboytes et al. |
| 2013/0123830 A1 | 5/2013 | Becking et al. |

(56) References Cited

U.S. PATENT DOCUMENTS

| | | |
|---|---|---|
| 2013/0144380 A1 | 6/2013 | Quadri et al. |
| 2013/0172925 A1 | 7/2013 | Garcia et al. |
| 2013/0172976 A1 | 7/2013 | Garcia et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |
| 2014/0012307 A1 | 1/2014 | Franano et al. |
| 2014/0058420 A1 | 2/2014 | Hannes et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0316012 A1 | 10/2014 | Freyman et al. |
| 2014/0371734 A1 | 12/2014 | Truckai |
| 2015/0216684 A1 | 8/2015 | Enzmann et al. |
| 2015/0250628 A1 | 9/2015 | Monstadt et al. |
| 2015/0272590 A1 | 10/2015 | Aboytes et al. |
| 2015/0313737 A1 | 11/2015 | Tippett et al. |
| 2015/0327843 A1 | 11/2015 | Garrison |
| 2015/0342613 A1 | 12/2015 | Aboytes et al. |
| 2016/0022445 A1 | 1/2016 | Ruvalcaba et al. |
| 2016/0030050 A1 | 2/2016 | Franano et al. |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |
| 2019/0282242 A1 | 9/2019 | Divino et al. |
| 2019/0343532 A1 | 11/2019 | Divino et al. |
| 2020/0061099 A1 | 2/2020 | Li et al. |
| 2020/0367904 A1 | 11/2020 | Becking et al. |

FOREIGN PATENT DOCUMENTS

| | | |
|---|---|---|
| CN | 102083493 A | 6/2011 |
| DE | 1283434 B | 11/1968 |
| DE | 102008028308 A1 | 4/2009 |
| DE | 102010050569 A1 | 5/2012 |
| DE | 102011011510 A1 | 8/2012 |
| DE | 102011102933 A1 | 12/2012 |
| EP | 0717969 A2 | 6/1996 |
| EP | 0743047 A2 | 11/1996 |
| EP | 0855170 A2 | 7/1998 |
| EP | 0775470 B1 | 3/1999 |
| EP | 1188414 A1 | 3/2002 |
| EP | 1637176 A1 | 3/2006 |
| EP | 1752112 A1 | 2/2007 |
| EP | 1813213 A2 | 8/2007 |
| EP | 1923019 A1 | 5/2008 |
| EP | 1942972 A1 | 7/2008 |
| EP | 1872742 B1 | 5/2009 |
| EP | 2208483 A1 | 7/2010 |
| EP | 2279023 A2 | 2/2011 |
| EP | 2363075 A1 | 9/2011 |
| EP | 2496299 A2 | 9/2012 |
| EP | 2675402 A2 | 12/2013 |
| FR | 2556210 B1 | 4/1988 |
| FR | 2890306 A1 | 3/2007 |
| JP | 11506686 | 6/1999 |
| JP | 2003520103 A | 7/2003 |
| JP | 2003524434 A | 8/2003 |
| JP | 2004049585 A | 2/2004 |
| JP | 2005522266 A | 7/2005 |
| JP | 2005261951 A | 9/2005 |
| JP | 2006506201 A | 2/2006 |
| JP | 2008521492 A | 6/2008 |
| JP | 2008541832 A | 11/2008 |
| JP | 4673987 B2 | 1/2011 |
| WO | 8800813 A1 | 2/1988 |
| WO | 9406502 A2 | 3/1994 |
| WO | WO 9509586 A1 | 4/1995 |
| WO | 9601591 A1 | 1/1996 |
| WO | WO 9726939 A1 | 7/1997 |
| WO | WO 9809583 A2 | 3/1998 |
| WO | WO 9902092 A1 | 1/1999 |
| WO | WO 9903404 A1 | 1/1999 |
| WO | 9908607 A1 | 2/1999 |
| WO | 9908743 A1 | 2/1999 |
| WO | WO 9905977 A1 | 2/1999 |
| WO | 9940873 A1 | 8/1999 |
| WO | WO 9949812 A2 | 10/1999 |
| WO | WO 9962432 A1 | 12/1999 |
| WO | 0057815 A1 | 10/2000 |
| WO | WO 0228320 A2 | 4/2002 |
| WO | WO 02071977 A2 | 9/2002 |
| WO | WO 03007840 A2 | 1/2003 |
| WO | 03011151 A1 | 2/2003 |
| WO | WO 03022124 A2 | 3/2003 |
| WO | 03037191 A1 | 5/2003 |
| WO | WO 03049600 A2 | 6/2003 |
| WO | WO 2004010878 A1 | 2/2004 |
| WO | WO 2004030575 A1 | 4/2004 |
| WO | WO 2004066809 A2 | 8/2004 |
| WO | WO 2004087006 A2 | 10/2004 |
| WO | WO 2005018728 A2 | 3/2005 |
| WO | WO 2005030093 A1 | 4/2005 |
| WO | WO 2005115118 A2 | 12/2005 |
| WO | WO 2005117718 A1 | 12/2005 |
| WO | 2006034149 A2 | 3/2006 |
| WO | 2006034166 A2 | 3/2006 |
| WO | WO 2006026744 A1 | 3/2006 |
| WO | WO 2006052322 A2 | 5/2006 |
| WO | WO 2006091891 A2 | 8/2006 |
| WO | 2006119422 A2 | 11/2006 |
| WO | WO 2006127005 A1 | 11/2006 |
| WO | 2007006139 A1 | 1/2007 |
| WO | 2007047851 A2 | 4/2007 |
| WO | 2007076480 A2 | 7/2007 |
| WO | 2007095031 A2 | 8/2007 |
| WO | WO 2007121405 A2 | 10/2007 |
| WO | WO 2008022327 A2 | 2/2008 |
| WO | 2008074027 A1 | 6/2008 |
| WO | 2008109228 A2 | 9/2008 |
| WO | WO 2008151204 A1 | 12/2008 |
| WO | WO 2008157507 A2 | 12/2008 |
| WO | 2009014528 A1 | 1/2009 |
| WO | 2009076515 A1 | 6/2009 |
| WO | 2009132045 A2 | 10/2009 |
| WO | 2009135166 A2 | 11/2009 |
| WO | WO 2009134337 A1 | 11/2009 |
| WO | 2010009019 A1 | 1/2010 |
| WO | 2010027363 A1 | 3/2010 |
| WO | 2010028300 A1 | 3/2010 |
| WO | WO 2010030991 A1 | 3/2010 |
| WO | 2010077599 A1 | 7/2010 |
| WO | 2010147808 A1 | 12/2010 |
| WO | 2011057002 A2 | 5/2011 |
| WO | 2011057277 A2 | 5/2011 |
| WO | WO 2011066962 A1 | 6/2011 |
| WO | 2011095966 A1 | 8/2011 |
| WO | WO 2011130081 A1 | 10/2011 |
| WO | 2011153304 A1 | 12/2011 |

(56) References Cited

FOREIGN PATENT DOCUMENTS

| | | |
|---|---|---|
| WO | 2012034135 A1 | 3/2012 |
| WO | 2012068175 A2 | 5/2012 |
| WO | 2012112749 A2 | 8/2012 |
| WO | 2012166804 A1 | 12/2012 |
| WO | 2013112944 A1 | 8/2013 |
| WO | 2013138615 A2 | 9/2013 |
| WO | 2013138615 A3 | 9/2014 |
| WO | WO 2017074411 A1 | 5/2017 |
| WO | WO 2018051187 A1 | 3/2018 |

OTHER PUBLICATIONS

Brilstra, et al., Treatment of Intracranial Aneurysms by Embolization with Coils: A Systematic Review, Stroke, Journal of the American Heart Association, 1999, vol. 30, pp. 470-476.

Ferguson, Gary, Physical Factors in the Initiation, Growth and Rupture of Human Intracranial Saccular Aneurysms, J. Neurosurg., Dec. 1972, vol. 37, pp. 666-667.

Geremia, et al., Embolization of Experimentally Created Aneurysms with Intravascular Stent Devices, ANJR American Journal of Neuroradiology, Au 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosit, Ann of Biomedical Eng., 1997, vol. 25, pp. 460-469, Buffalo, NY.

Lieber, et al., The Physics of Endoluminal Stenting in the Treatment of Cerebrovascular Aneur sms, Neurolo ical Research, 2002, vol. 24, Issue Supplement 1, pp. S32-S42.

Moss, et al., Vascular Occlusion with a Balloon-Expadable Stent Occluder, Radiology, May 1994, vol. 191, Issue 2, pp. 483-486.

Pereira, Edgard, History of Endovascular Aneurysm Occlusion, Management of Cerebral Aneur sms, 2004, pp. 11-26.

Qureshi, Adnan, Endovascular Treatment of Cerebrovascular Diseases and Intracranial Neo lasms, The Lancelet, Mar. 2004, vol. 363, pp. 804-813.

Steiger, Pathophysiology of Development and Rupture of Cerebral Aneurysms, Acta Nurochirur ica, Mar. 1990, vol. Suppiementum 48, Pages in 62 pages.

Tenaglia, et al., Ultrasound Guide Wire-Directed Stent Deployment, Duke University Medical Center, De artment of Medicine, 1993 USA.

Hill, S., et al., Initial Results of the AMPLATZER® Vascular Plug in the Treatment of Congenital Haert Disease, Business Briefing: US Cardiology 2004.

Ronnen, H. R., Amplatzer® Vascular Plug Case Study, Closure of Arteriovenous Fistula Between Deep Femoral Artery and Superficial Femoral Vein, AGA Medical Corporation, May 2007.

\* cited by examiner

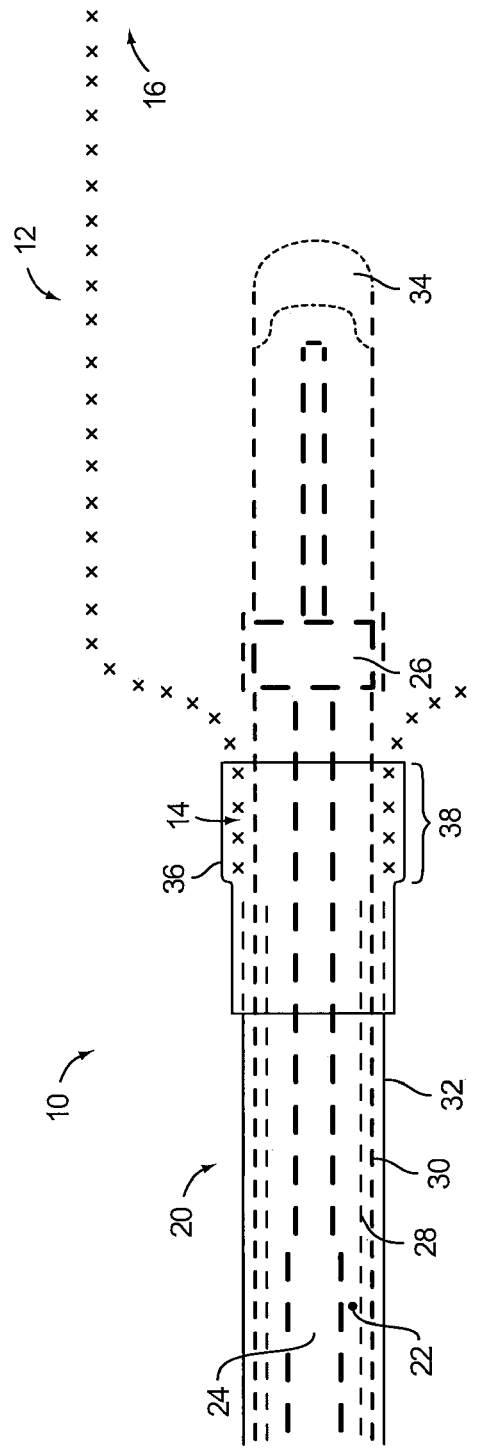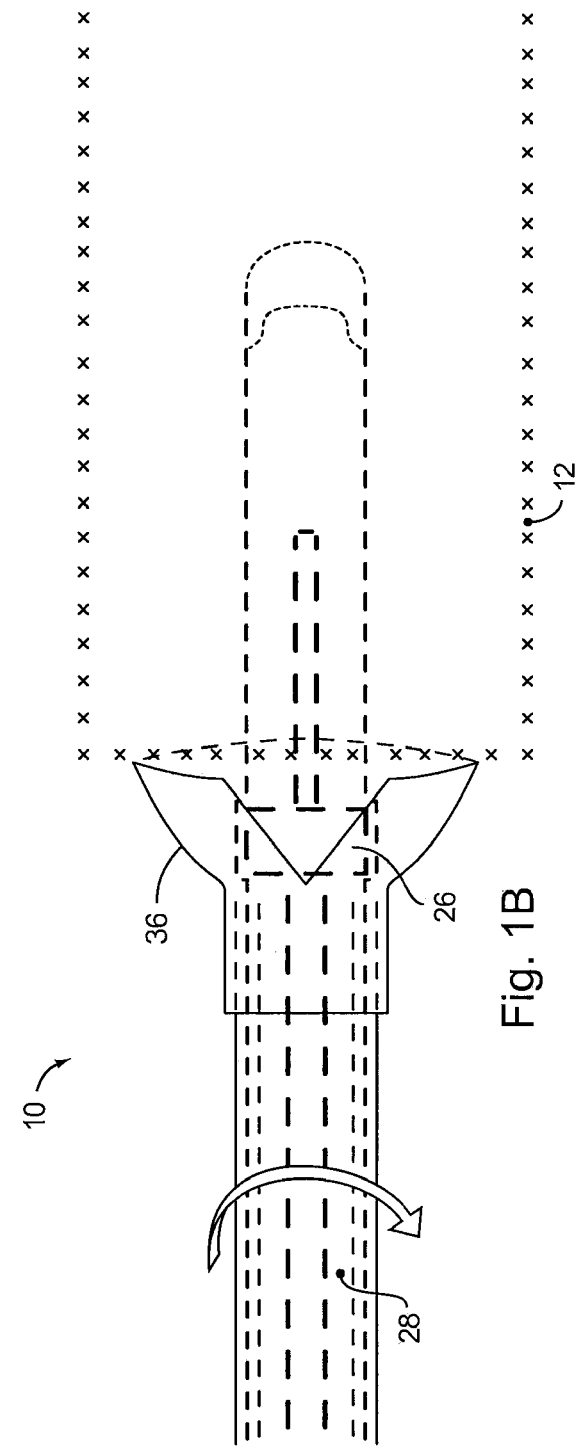

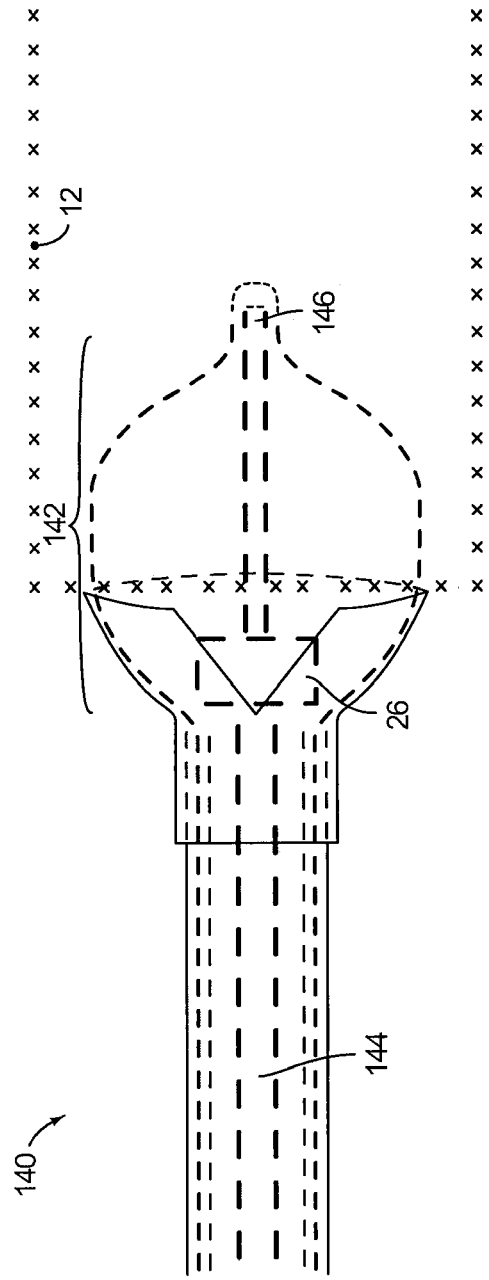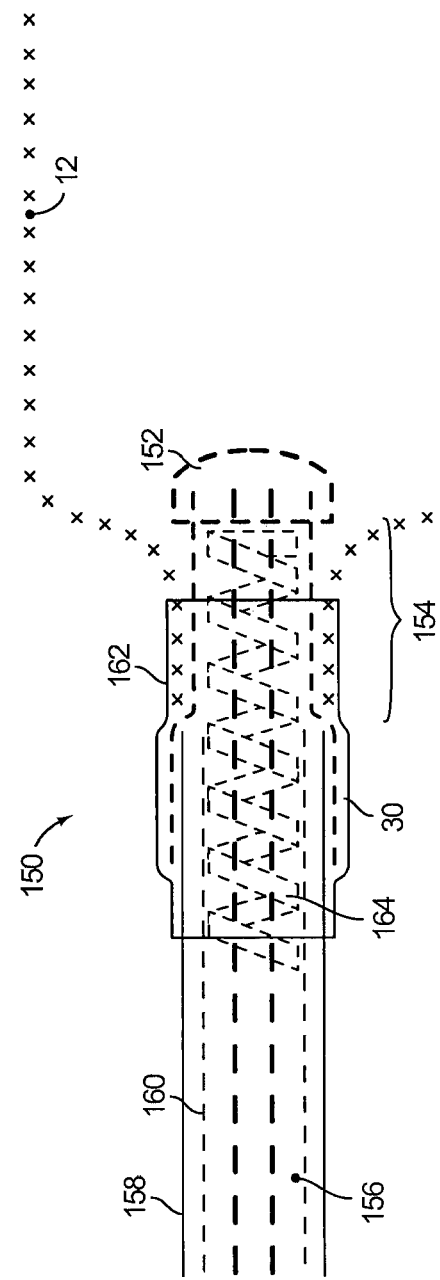

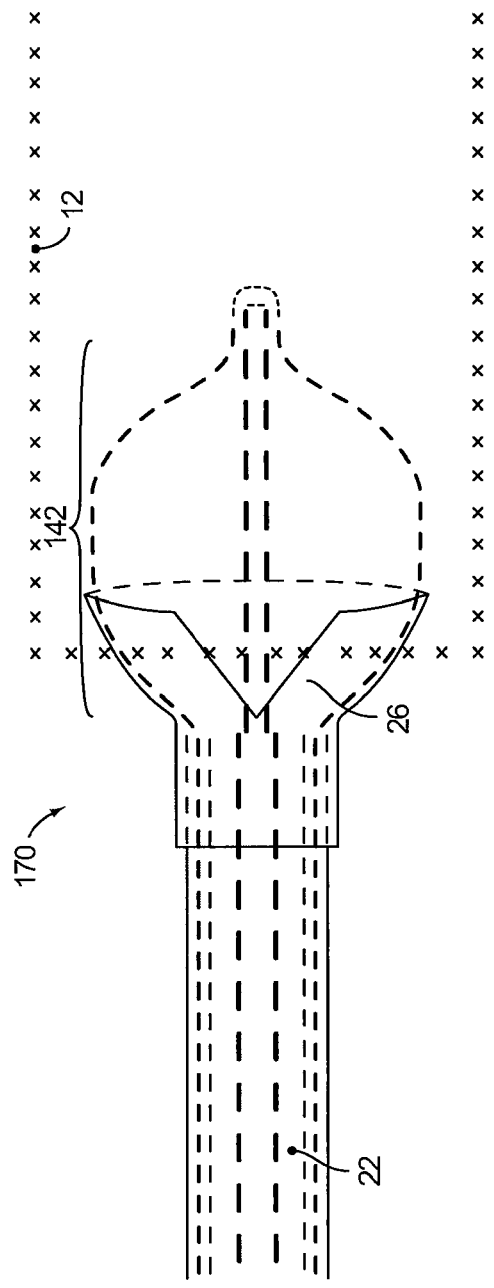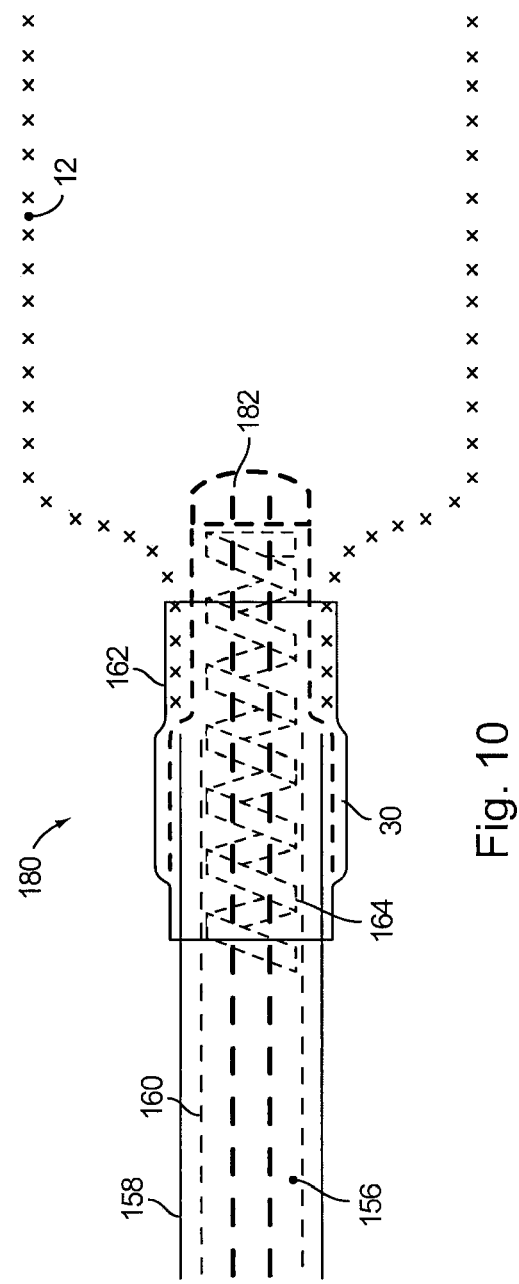

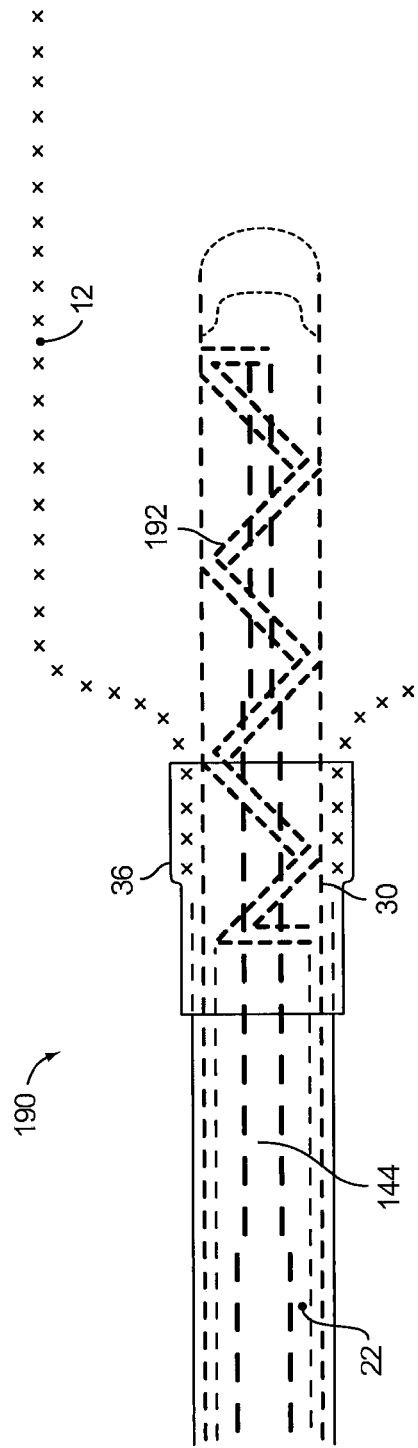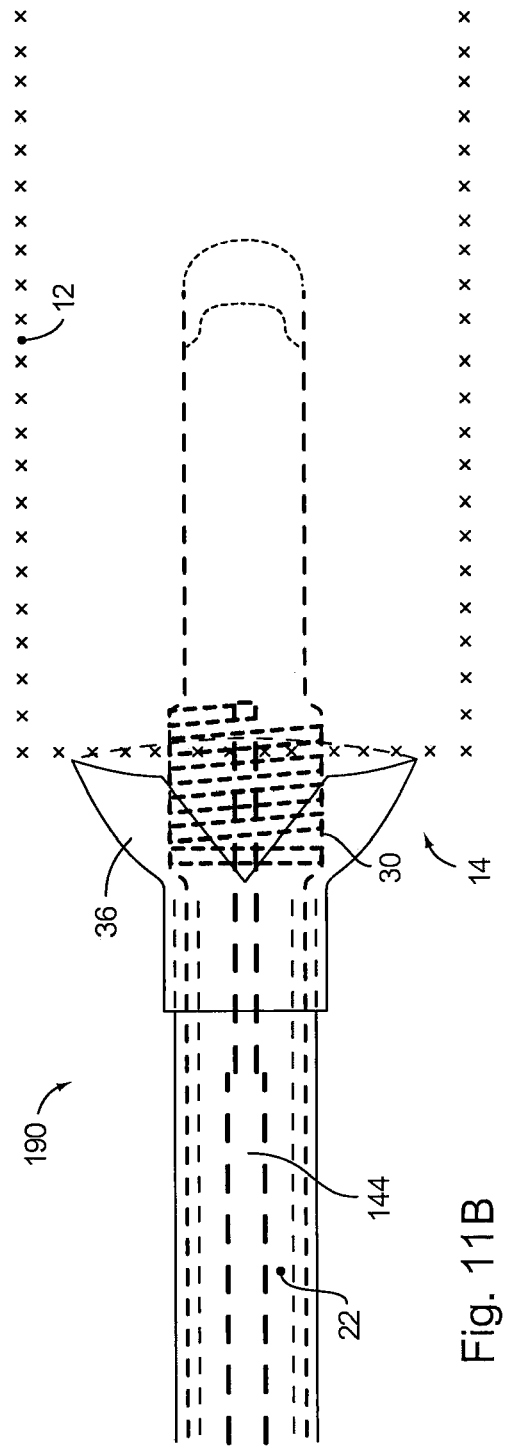

BRAID IMPLANT DELIVERY SYSTEMS

CROSS-REFERENCE TO RELATED APPLICATIONS

The present application is a continuation of U.S. patent application Ser. No. 15/598,357, filed May 18, 2017, which is a divisional of U.S. patent application Ser. No. 12/465,475, filed May 13, 2009, now U.S. Pat. No. 9,675,482, which claims the benefit of U.S. Provisional Patent Application Ser. Nos. 61/052,756, filed May 13, 2008, and 61/083,959, filed Jul. 28, 2008, the disclosures of which are incorporated herein by reference in their entireties.

FIELD OF THE INVENTION

The subject matter described herein relates generally to systems, devices and methods for the delivery of textured (e.g., braided or woven) medical implants.

BACKGROUND

Mainstream clinical practice in endovascular treatment of intracranial aneurysms has changed little since the 1990's when vaso-oclusive coil use became widespread. Certainly, improved catheters and other auxiliary devices (e.g., stents) have helped make coiling procedures safer and/or more effective. However, the art in achieving adequate and appropriate aneurysm coil packing is best accomplished by the most highly skilled physicians.

Where practicable, aneurysm exclusion by cover-type devices (e.g., as described in U.S. patent application Ser. No. 12/397,123 (US Publication No. 2009/0319023) to the assignee hereof) may be preferred. Certain other groups are attempting to shift the paradigm away from intra-aneurysm coil packing to achieve embolization via deployment of an extra-aneurysm flow disruptor/diverter stent in the parent vessel. These densely braided devices and/or multiple braid devices layered upon one another are placed in the parent vessel across the neck of an aneurysm with the intent to alter hemodynamics so as to effect embolization.

US Patent Publications 2006/0271149 and 2006/0271153, assigned to Chestnut Medical Technologies, Inc., disclose delivery systems such braid-type stents. In one example system, a coil socket holds the distal end of the implant until this end is released during delivery catheter retraction with grippers holding the proximal end of the implant. These grippers are able to maintain contact with the proximal end of the implant through compression by the delivery catheter sleeve surrounding the grippers. Upon sleeve withdrawal, the grippers release the proximal end of the stent.

System miniaturization of the referenced system(s) is limited by the gripper configuration. Also, the lack of an active release mechanism for detachment from the distal socket presents issues of inadvertent deployment and/or non-optimal control.

Accordingly, there remains a need for each of more robust/reliable and/or more compact systems for advanced braid-type implant delivery. The present invention offers such systems with various advantages as presented herein and others as may be apparent to those with skill in the art.

SUMMARY OF THE INVENTION

The systems, methods and devices described in this section and elsewhere herein are done so by way of exemplary variations or embodiments. These examples are provided to aid in the description of the inventive subject matter and are in no way intended to limit the inventive subject matter beyond the express language of the claims.

The implant is preferably (i.e., has been selected as but is not necessarily) a stent or stent-like device and is held onto the delivery system by one or more releasable tubular covers. Each such cover is typically limited in length to envelop a relatively short length of the implant. Overlap between the members (i.e., cover and implant) is typically between about 1 mm and about 5 mm. More preferably, the overlap is between about 1.5 mm and about 3 mm. Accordingly, the cover(s) can be characterized as mini-sheath(s).

Implant release from the delivery system is accomplished by rupturing, tearing or otherwise splitting the mini-sheath cover(s). The cover(s) may be perforated or notched to promote breakage/rupture/tearing upon application of an expansive force.

Each mini-sheath is opened by expansive mechanical action generated by retraction of a core member. The core member may be user-actuated from a handle, by shape memory alloy (SMA) action upon heat application, or operate otherwise.

The expansion action is transmitted through the implant to force open the cover. In some examples, a sledge or wedge-type feature is pulled under the implant, thereby expanding it against the cover. In other examples, an expandable body under the implant forces the cover to open. Some examples described herein rely on both types of action.

The expander (e.g., in the form of a wedge or an expandable body) may contact the implant directly. Alternatively, an intermediate layer of material may be provided. Such a layer can be used to avoid implant damage, where the intermediate layer or member takes any abrasion, etc. along its inner surface—in effect shielding the implant matrix—and expands in unison with the implant to open the cover. The intermediate layer may also, or instead, be selected to provide a surface against which the implant is frictionally locked when constrained by the cover.

Such a lock relies on a high degree of surface friction between the implant and an underlying surface to resist longitudinal/axial motion of the implant (in its contracted state) along the longitudinal axis of the delivery device or sleeve. Substantial surface friction between implant and the underlying surface will prevent the implant from sliding relative to the underlying surface, preventing the implant from decreasing in length (i.e., foreshortening) and radially expanding. Although the term "lock" can be used, it should be understood that the implant is not locked from all movement in an absolute sense, as the implant can be forced from the lock should sufficient force be applied to overcome the surface friction. Rather, the implant is preferably locked in place sufficiently to resist the implant's own bias towards expansion (if any), to resist bias applied by a secondary expansion device (if any), to resist forces applied against the implant while maneuvering within the patient's vasculature (e.g., forces applied either by the delivery device or the patient's vasculature or blood flow), and/or to resist forces applied to the implant during any loading, unloading, or deployment procedures. Of course, one of skill in the art will appreciate that the degree of surface friction necessary to achieve the state of frictional lock will depend on the specific delivery device implementation and intended application(s).

When a frictional lock is relied upon to retain the implant on the delivery system until release, the implant preferably has textured surfaces (which may be continuous or disconnected) where it is intended to be secured to the delivery system by the mini-sheath(s). The surface(s) is/are preferably present about the entire inner periphery of the implant, but can also be located in limited regions generally corresponding to the interface regions of the sleeve.

In a preferred implementation, both the intermediate body and the implant comprise braid. However, other textured surfaces can be formed on either body by altering its surface to create a textured pattern, e.g., by etching, grinding, sanding, and the like. Still other textured surfaces can be formed by applying a high-friction coating to the body. Of course, any combination of these can also be used (e.g., a braid implant on a patterned underlying surface, etc.). Other optional details and discussion of the frictional interface between the implant and delivery system body may be taken from U.S. patent application Ser. No. 12/412,731, filed on Mar. 27, 2009 and titled "Friction-release Distal Latch Implant Delivery System and Components," which is incorporated by reference for this purpose.

In another variation, instead of using a frictional lock generated between the implant and an underlying member to maintain the implant on the delivery system, an interlocking approach with the mini-sheath may be relied upon. In one example, the mini-sheath may comprise heat shrink that is entrained with the implant. Such interlocking may be assisted by vacuum forming while shrinking.

The interlock may alternatively, or additionally, be improved by including interface features on/in the implant around which the heat shrink forms. In an example where the implant comprises braid, some or all of the ends of the braid may be formed into ball ends (e.g., by laser application to from 0.003-0.005 inch diameter bodies) that the heat shrink can grasp. As a corollary advantage, these bodies may be radiopaque. Alternatively, radiopaque bands or coils that are crimpled, welded, soldered or otherwise affixed the implants ends could serve as retention features for the mini-sheath(s). These may be affixed only at the ends, or at intermediate points (e.g., to indicate a central section of increased density or any included cover).

In a preferred embodiment, the implant is a braided device with a braided surface about its entire exterior. The implant's number of wires, braid angle, pore size, profile, diameter, etc. may range in size. The braid may be metallic (as in NiTi, St. Steel, CoCr, other Ti and/or Zirconium alloy. etc.), polymeric, of hybrid construction or otherwise. Preferred variations may be formed of Nitinol. The alloy is preferably superelastic at body temperature. The metal may be a binary alloy or a ternary alloy to provide additional radiopacity. Alternatively, platinum or tantalum DFT Nitinol or platinum or tantalum wires may be included in the braid.

The density of the device is paramount in applications where braid itself is intended to affect blood flow, allowing thrombosis outside the implant to occlude a site. High density braid/mesh is typically required for such applications. Namely, braid having at least about 48 ends, typically set at about 90 degrees or greater, in diameters from about 4 to about 8 mm may be employed. At larger diameters (e.g., about 6 mm to 12 mm or more), more wire ends (e.g., common braider-size multiples of 64, 72 or 96) may be employed in forming the implants. Still higher typical wire counts may be employed. Moreover, 3-D braiding technology (such services are provided by 3Tex, Inc.) may be employed in forming the implant braid matrix.

A range of wire sizes or combination of wire sizes may be employed, typically ranging from about 0.0008 to about 0.0015 inch, and up to about 0.003 inches depending on desired delivery profile. A single braid tube may have all wires the same diameter, or may have some wires of a slightly thicker diameter to impart additional strength to the braid layer. The thicker wires impart greater strength to the implant without significantly increasing the device delivery profile, with the thinner wires offering some strength while filling-out the braid matrix density.

At least when employing Nitinol wire, to improve implant wire corrosion resistance and/or biocompatibility after any heat setting shape, the implants may be etched in "AYA" Sulfamic Acid solution, then passivated in Nitric acid solution. Alternatively or additionally, pre-etched and/or polished wire may be employed in braiding the implant matrix. Shape setting the braid in the implant shape may be performed in an oven/furnace, a fluidized bath or salt pot. All such processing is within the knowledge of those with ordinary skill in the art.

In some cases, the braid may incorporate polymeric fibers into the braid matrix—biodegradable (e.g., PLA/PGLA) or otherwise. Likewise, while the implants advantageously comprise include polymeric fill fiber, the entire braid may instead comprise polymer—especially high strength biodegradable polymer such as MX-2 (MAX-Prene), synthetic absorbable monofilament (90/10 Glycolide/L-Lactide) and/or G-2 (Glycoprene), synthetic absorbable monofilament (Glycolide (PGA), E-Caprolactone (PCL), Trimethylene Carbonate (TMC) Copolymer) that is heat set into shape (e.g., at 110 degrees centigrade for an hour).

Whatever the material, the braid may be uniform, or it may be configured with a higher density center "patch" or circumferential section. If so, such a section will typically be located at the center of the device. Or, it may be offset distally. Moreover, a coating—such as urethane, etc. may be set over the implant in similar fashion. Still further configurations of implants having grafts, coatings (e.g., lubricious, drug-eluting, and the like) or other non-textured surfaces present on the exterior of the implant are possible. See, e.g., U.S. Pat. No. 4,416,028 to Eriksson, et al. Coatings, such as those available through NiCast, Inc. (Israel) or Medical Device Works (Belgium), may be used for such purposes, as well as others. Hydrogel coating also offers an appealing option, such as a hydrogel-based polymer network capable of entrapping therapeutic agents as described in U.S. Pat. No. 6,905,700 to Won et al.

The implant may include radiopaque markers as described above, or as described in either of U.S. patent application Ser. No. 12/412,731, filed on Mar. 27, 2009 and titled "Friction-release Distal Latch Implant Delivery System and Components," or 61/177,847, filed on May 13, 2009 and titled "Absorbable Braid Implants and Delivery Systems," each incorporated herein by reference in its entirety.

The implant is expandable from a contracted state to an expanded state, and preferably self-biased towards the expanded state (i.e., "self-expanding" as understood by those with skill in the art. Generally, expansion results in lengthwise shortening of the implant. Especially in braid-type implants, holding the end portions of the implant stretched apart from each other (as in at least one exemplary variation herein) can cause the implant to be maintained in a contracted state, without the need to radially restrain the entire implant (such as with a full body sheath).

Certain variations of the subject invention take advantage of this action. One such example releasably captures both ends of the implant so as to offer potential for independent navigation, especially when an optional atraumatic tip is incorporated in the design. Precision placement of the implant is achieved by predictable mini-sheath release upon rupture by contact with an inner floating wedge. By contracting the system, the floating wedge contacts each mini-sheath region at substantially the same time. However, the mini-sheath regions can be staged to release independently, for example, by using sheaths with varying thicknesses or by other means readily apparent to those of ordinary skill in the art.

System flexibility can be optimized by using multi-segment (e.g., rings) wedge members. Alternatively, a selectively slit hypotube (e.g., Nitinol, resembling a segment of a SYNCHRO guidewire) or a coil spring (e.g., stainless steel or Nitinol) may be used. The coil spring can be tightly packed or include gaps that bottom-out upon compression. In any case, the ends of the spring are optionally be held together (e.g., by soldering) or set within jacket(s).

However constructed, the wedge member(s) may underlie a braid shaft preferably attached adjacent an atraumatic tip, and running the full length of the delivery system. As discussed above, such a braid shaft offers an advantageous interlock with a braid implant to provide for robust stretch to a reduced diameter profile. Still further, the section of braid under the implant may be used to provide a mechanical expansion "balloon" effect to assist in splitting the mini-sheaths when compressed.

In an alternative construction, no wedges are provided, but such a braid expander is relied upon alone to open the mini-sheaths. Likewise, other constructions that expand when axially compressed are contemplated for rupturing the implant covers, including: coils, volume-incompressible polymer bodies (e.g. one or more urethane tubes), micro-machined (e.g., etched, EDM or laser-cut) metal lattices, etc.

Regardless, when deployed—as typical—in a vessel undersized relative to the implant, the system offers the potential for unique operation. In one mode of delivery, the stent is compressed until it reaches the vessel wall. After advancing the implant to a treatment site, the implant is compressed to achieve tissue apposition. With the body of the implant so-anchored, the end being moved (typically the distal end is retracted and the proximal shaft held stationary) causes the braid to evert and roll inward.

Upon release, the result is an implant having a substantially predictable (user selected) in-situ length, with a double-layer section of the braid. Such a feature is unique to delivery of braid-type implants because their length is typically dictated by vessel diameter. The current system, instead, allows not only for more precise placement than known delivery systems (typically sheath-based), but also a specified final implant length. In another mode of delivery, sizing may be selected to simply provide one layer. Either way, maximum braid density (e.g., as useful for flow-disruption/occlusion application) is achievable through the compressed delivery of the braid implant.

In an alternative configuration, the delivery system includes only one implant release latch. Such a device will be used in coordination with a microcatheter.

The latch may be configured for the proximal end or the distal end of the implant. In any case, precision placement of the implant is once-again achieved by predictable mini-sheath release upon its rupture. The rupture may be driven by a wedge member, an expandable braid or coil section, other means or a combination of such means.

However configured, to facilitate loading into a microcatheter for navigation to a treatment site and use, a loading sheath may be provided over at least a portion of the implant as typical. To assist in tracking within the catheter, delivery system may include a passive socket in which to receive the distal end of the implant and/or include a floppy tip.

Some of the delivery system architectures advantageously incorporate a braided tube that runs substantially the length of the system. With a jacket over the proximal portion, the construction provides a stable shaft. The jacket for the braided shaft may simply be an extension of the mini-sheath heat shrink material. At least one distal section of this braid is exposed to serve at least as a frictional interface member with the implant. In one example, it is only the interface. In another example, it provides both the implant interface and one or more expander element(s).

A jacketed braid shaft can be configured to be highly pushable, torqueable and kink-resistant. Moreover, in a braided configuration, the composite sleeve can have its PIC (Per Inch Crosses) varied along its length to provide enhanced distal flexibility. In other words, the sleeve may be tuned/modified as a catheter-like subcomponent of the system. In an alternative configuration, an elongate polymeric, metallic or metal alloy shaft can be used with section to interface with the implant.

Similarly, the core member can also be configured for enhanced flexibility. For example, the core member may have one or more successively tapered regions near or adjacent to its distal end, like a typical guidewire. In some examples, the core member has column strength (i.e., as in a wire) to allow tip extension; in others, it may be a tensile-capable member alone (e.g., as in a fiber or yarn). Both the core member and the sleeve can comprise an elastic or superelastic material such as stainless steel, NiTi, CoCr, other alloys, polymeric materials, and the like.

The sleeve jacket and/or implant restraint sheaths can, for example, be formed by heat-shrinkable tubing. The heat-shrink for the covers, and the jacket described above, may be PE (polyethylene), PET (polyester), or the like. PI (polyamide), FEP, PEEK and other materials may also be advantageously employed in some cases. The mini-sheath/sleeve may be perforated or notched to promote breakage/rupture.

It is typically thin-walled heat shrink (e.g., about 0.0003 to about 0.0005 inch wall thickness PET). With or without the underlying braid frictional lock "Velcro" effect (and instead using a discrete proximal shaft comprising, e.g., PEEK or Nitinol) the mini-sheaths preferably comprise heat-shrink tubing that recovers to engage the implant. Thin wall (e.g., about 0.001 inch or less) PET is suitable for such retention and release as shown and described. Still, other materials may be used for the mini-sheaths, just as any suitable conventional material may be employed for the core member (e.g., NiTi, stainless steel) and other system components including those referenced above.

Depending on the device configuration, the delivery system inserted into the patient's vasculature may be directly navigated to a treatment site using conventional techniques just as if it were a guidewire. Alternatively, it may simply be passed through a catheter after exchange with a guidewire. Accordingly, for neurovascular applications, the system is advantageously sized to cross either an 0.021 or 0.027 inch microcatheter. The device is feasibly made with as small as about an 0.018 inches diameter. It may still be useful at larger sizes (especially for other applications—such as in the coronary or peripheral vasculature) as well.

After advancement to the treatment site, the implant is delivered by releasing or disengaging the implant. The implant may be so-delivered for a number of purposes. With a braided stent, at higher densities, it may be used to disrupt/divert the flow to treat an aneurysm or fistula. The implant may be delivered across a lateral wall aneurysm to effect flow disruption alone or with multiple devices. It may be also be used as a "coil jailer" by first trapping a micro-catheter between the stent and a vessel wall and delivering coils into an aneurysm. It could be placed along one branch of a bifurcation to disrupt flow to a bifurcation/trifurcation aneurysm or offer a platform for retaining coils therein. It may be used as a liner, followed by placement of a tube-cut stent within it when stenting diseased saphenous vein grafts.

Other possibilities exist as well or will be apparent to those of ordinary skill in the art. The inventive subject matter provided herein includes these methods, systems and devices for practicing these methods, and methods of manufacturing those systems and devices.

BRIEF DESCRIPTION OF THE DRAWINGS

The details of the inventive subject matter set forth herein—both as to structure and operation—may be appreciated, in part, by study of the accompanying figures, in which like reference numerals may refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely. Variation from the embodiments depicted is, of course, contemplated. Moreover, details commonly understood by those with skill in the art may be omitted as will be understood in review of the figures. Of these:

FIGS. 1A and 1B are partial side views depicting an example embodiment of the implant delivery system with an implant attached to and released from the system, respectively.

FIG. 7 is a partial side view of a one-sided detachment system related to the double-sided system in FIGS. 3A-3C in it use of a wedge member and expandable braid section for cover release.

FIG. 8 is a partial side view of another one-sided wedge-plus-braid expander type system.

FIG. 9 is a partial side view of a system like that presented in FIG. 7 but without an expansion wedge.

FIG. 10 is a partial side view of a system like that presented in FIG. 8 but without an expansion wedge.

FIGS. 11A and 11B are partial side views depicting an embodiment of the implant delivery system utilizing a compactable coil for cover release with an implant attached to and released from the system, respectively.

Figure 2A:
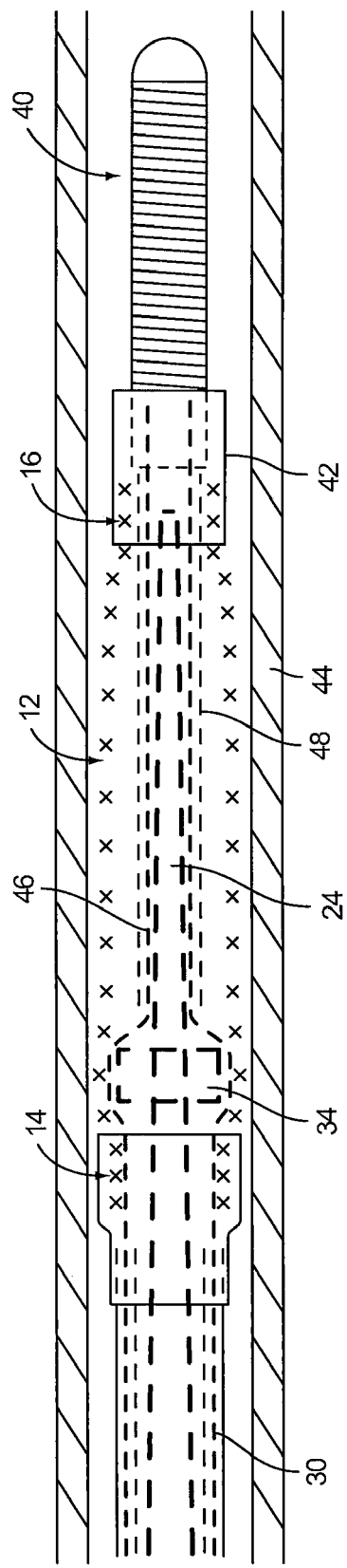
FIGS. 2A and 2B are partial side views depicting another example embodiment of the implant delivery system during progressive stages of deployment.

In these views, elements that are contained within other elements are shown in profile with broken lines. However, though sometimes partially obscured, the implant profile is illustrated using an "x x x x x" pattern for the sake of clarity.

DETAILED DESCRIPTION

Various exemplary embodiments of the invention are described below. Reference is made to these examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

Turning to FIG. 1A, it shows an implant delivery system 10 including an implant 12 comprising braid and having proximal 14 and distal ends 16 and a detachable pusher 20. An elongate sleeve 22 defines the pusher body. A core member 24 within the sleeve is connected to a wedge band 26. It may terminate at the wedge band or extend beyond it as shown. The core member 24 is optionally a wire (e.g., Stainless Steel or Nitinol), with one or more steps or taper as shown to offer graduated flex performance at least toward the distal end of the pusher 22 (up to or past the band 26). The band 26 may be cut from hypotube and be solder, welded or otherwise connected to the wire. It advantageously comprises steel or another hard material to avoid galling from contact with the braid. Alternatively, the "band" may comprise a few turns of a coil affixed to the core wire 24.

Sleeve (pusher) 22 comprises a liner 28 (e.g. PTFE lined Polyimide), tubular braid 30 (e.g., Stainless steel or Nitinol) and a jacket 32 (e.g., PET shrink tubing). Sleeve braid 30 extends under the implant proximal end 16, optionally, to terminate beyond core member 24 with a polymeric soft tip 34.

Mini-sheath or cover 36 holds the implant in a state of frictional lock with braid layer 30 along an overlap zone 38. This engagement is maintained until the core member 24 is withdrawn as illustrated in FIG. 1B. This action drives the wedge 26 under the engaged portion of the implant causing it to expand and tear, crack or otherwise rupture cover 36 open. Self-expansion of the implant effects release, and/or the pusher is simply withdrawn, to relieve any further interference. To ensure disengagement before removal, a 90 to 180 degree turn of the system may be advisable because the cover will typically (though not necessarily) split only along one side. Even without the turn, however, the lock holding the implant to the pusher is released allowing withdrawal with the implant in place.

Because the core member 24 in this variation of the invention is actuated only in tension, it may comprise a polymeric filament of fiber (e.g., Vectran or Spectra fiber), in which case the core member 24 is advantageously knotted to retain band 26, with optional potting with glue (e.g. 4014 LOCTITE). Delivery system flexibility can be maximized in this fashion, with any changes in stiffness developed along the body of the pusher (e.g., by changes to the braid and/or jacketing).

Figure 2B:
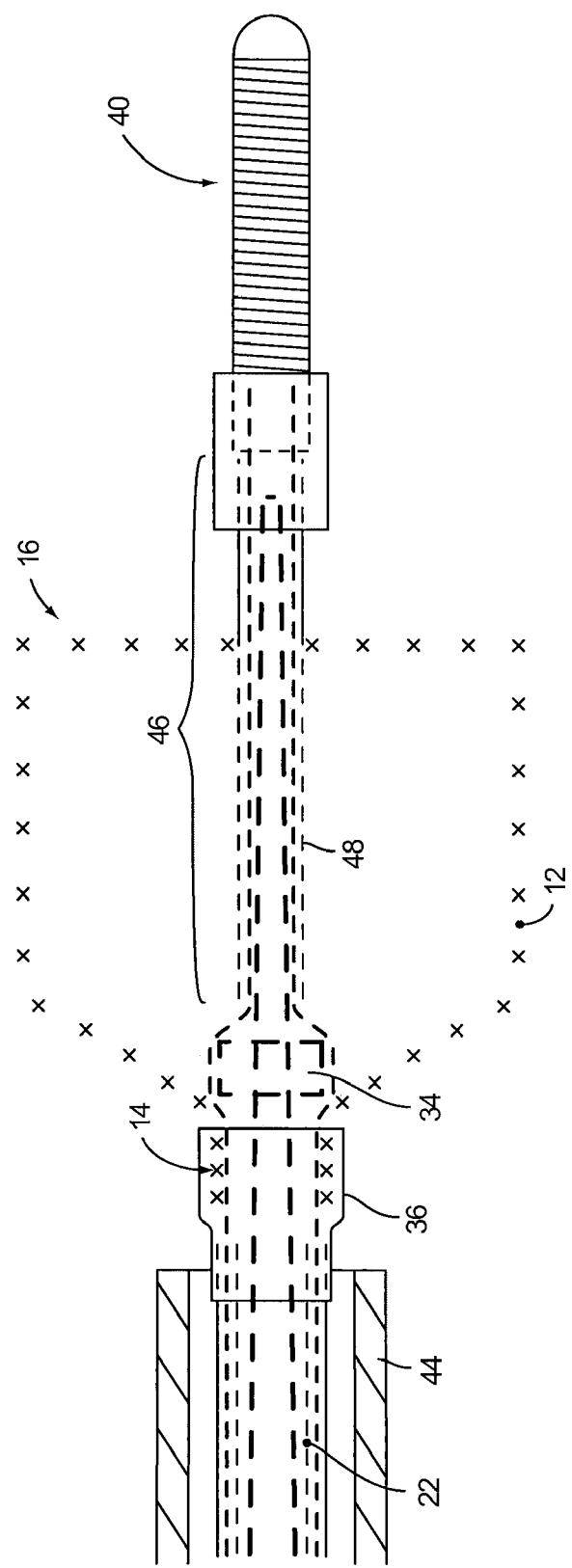

FIGS. 2A and 2B show a variation of the system in FIGS. 1A and 1B in which the intermediate braid layer 30 extends to secure a coil tip 40 and a cap or socket 42 for the implant distal end 16. For attachment to the coil tip 40, some of the braid wires may be trimmed-out with the remainder acting as a core to the tip. Such a tip may improve device tracking in a catheter. Setting the distal end of the implant in a socket may offer similar advantages.

When inside a catheter 44 (transferred thereto via a loading sheath as conventionally accomplished) the distal end of the implant 12 is protected within the cap 42. Upon exit from the catheter 44, the implant 12 is partially unconstrained and is able to expand so as to pull-out of the socket 42. Because no distal lock is provided in this variation of the invention, the cap 42 may comprise any of PI, PET or other tubing. No shrink onto the implant is necessary or desirable.

Braid extension 46 is optionally covered by a jacket 48 (e.g., with PTFE or PET shrink tubing or otherwise) to maintain dimensional stability of this body. Extending the jacket 48 underneath the distal end 16 of the implant 12 may also help ensure release as intended and illustrated in FIG. 2B when the implant 12 is free of the catheter 44.

Figure 3A:
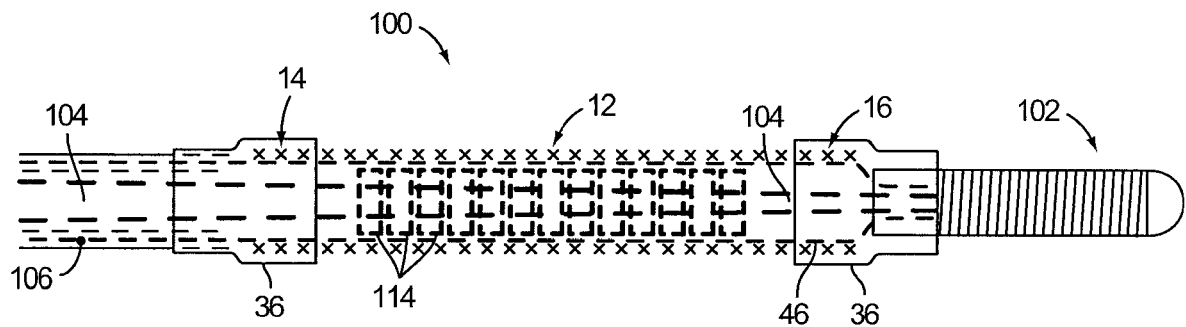
FIGS. 3A-3C are partial side views depicting yet another example embodiment of the implant delivery system during progressive stages of deployment.
Figure 3B:
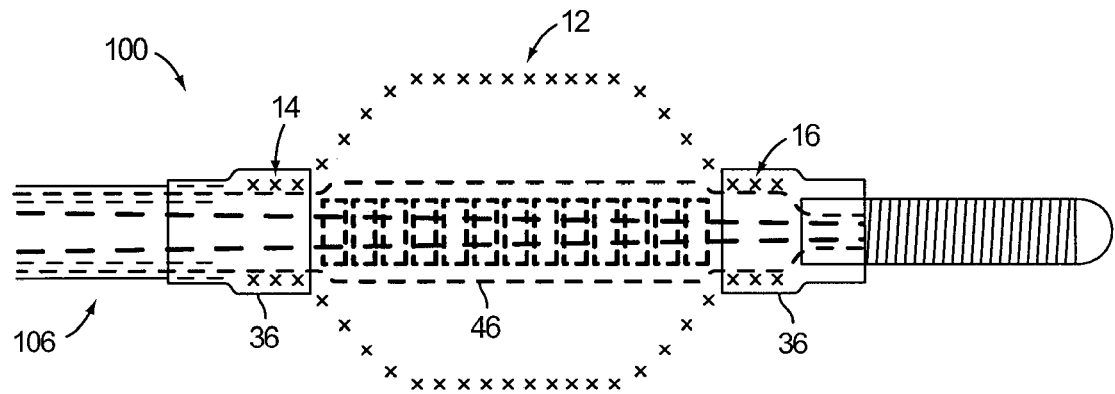
Figure 3C:
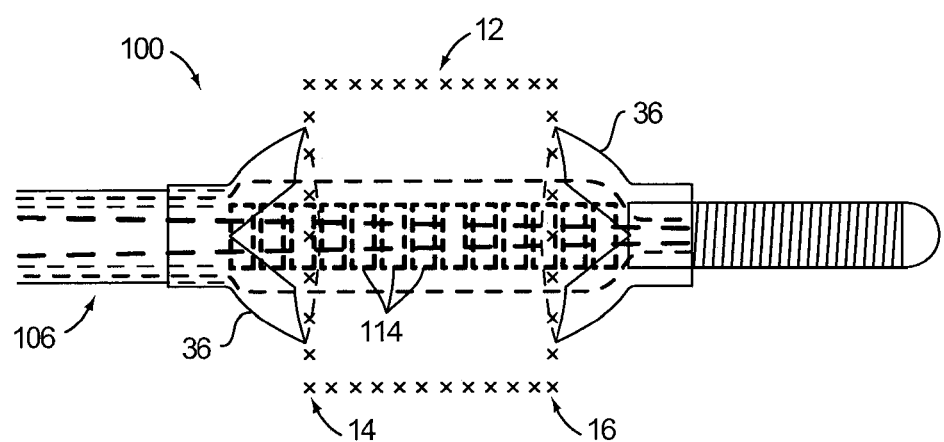

FIGS. 3A-3C are partial side views depicting yet another example embodiment of the implant delivery system during progressive stages of deployment. While the previous examples only held one end of the implant in a locked arrangement, this delivery system 100 releasable captures both ends of the implant.

In this case, atraumatic tip 102 is connected to core wire, or member, 104 received within sleeve 106. Braid extension section 46 is preferably similarly attached. In this manner, when the core member 104 is withdrawn (compare FIG. 3A and FIG. 3B), the braid extension section 46 expands. This expansion may serve either of one or two purposes. In the variation shown, it may simply provide clearance for the floating expander wedge member(s) 108, allowing them to move into position to force open each of the proximal and distal covers 110, 112 (in a similar fashion to that described in reference to FIGS. 1A and 1B. Still further, braid section 46 can itself operate as an expander to open the covers 110, 112.

In any case, when the compressive action continues (by withdrawal of core member 104 and/or advancement of sleeve/shaft 106), the wedges 108 are driven fully under the covers 110, 112 to break them open and allow implant release. Cover release may occur substantially simultaneously. Alternatively, the action can be staged. In some applications it may be desirable to open the proximal end first; in others the distal first (especially for potential recapture purposes).

Figure 5A:
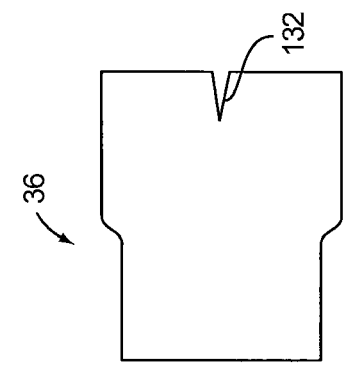
FIGS. 5A and 5B are detail illustrations of various mini-sheath/cover construction options to facilitate release.
Figure 5B:
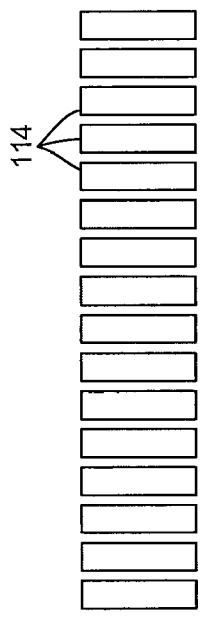

One way in which to accomplish sequential release is to utilize different thickness material, different type of material and/or vary such parameters as discussed in connection with FIGS. 5A and 5B, below, so that one cover is more freeable than the other.

In any case, it will be appreciated that a unique feature of delivery system 100 is that two release points are actuated by a single user input. This approach allows for minimizing delivery system profile as compared to a system that might include additional concentric layers to achieve similar two-sided functionality.

Indeed, minimizing the crossing profile for such a system can be especially useful in instances where it is intended to be used as a navigable delivery system in itself, as an interventionalist would employ a guidewire. Either by actively extending the core wire or by originally locking it into such a configuration during manufacturing, a "wire-like" delivery system is offered as shown in FIG. 3A. Given its (optional) tip-to-tail braid construction and the full-length core wire, the system can be optimized for such use. Excellent torquability is possible given that there need be no joints. Nor are their any performance-sapping component crossovers. The system is arranged in a completely concentric fashion in the example shown.

Figure 4A:
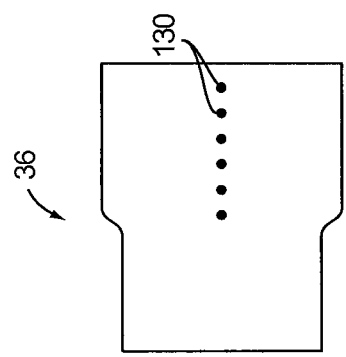
FIG. 4A-4C depict different wedge components as may be employed in the delivery systems, especially that shown in FIGS. 3A-3C.
Figure 4B:
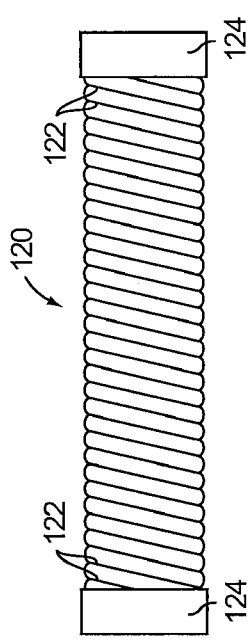
Figure 4C:
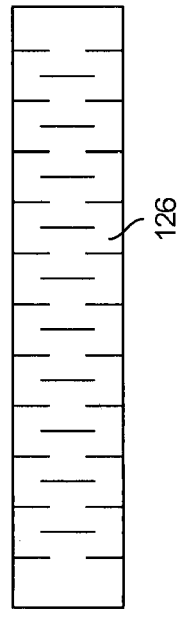

FIG. 4A-4C depict different wedge components as may be employed in delivery systems 100. FIG. 4A shows multiple bands 114. The bands may be independent (as shown) or interlocked in puzzle-piece fashion. FIG. 4B shows a coil spring 120. Turns 122 of the coil end are stabilized by soldered or welded zones 124. FIG. 4C shows a slit (e.g., by laser cutting or otherwise) hypotube 126. All of these options can provide excellent flexibility, while offering adequate resistance to compression during system actuation in order to work reliably. Moreover, the length of any of these members can be tuned/selected so as to match the implant mounted to the delivery system 100 and coordinate with its intended delivery action (e.g., simple linear deployment vs. the doubling-over approach described above).

Actually, in one variation, delivery system 100 can be configured to work without the bands at all. Specifically, braid section 46 can be tuned such that it severs as the only cover expander/expansion means necessary to effect release.

Whatever element(s) define as expansion means, treatment of the cover merits discussion itself. In some cases, the covers may simply be heat-shrunk down to the implant. As shown in FIG. 5A, however, it may be desirable to add perforations 130 (e.g., with a pin, laser or otherwise) to provide a weakened section or section(s) in the cover 36 to promote controlled rupture. In another approach, the cover 36 includes a notch or slit 132 to provide a point from which an intentional tear can propagate as shown in FIG. 5B. While not shown, the cover could alternatively be scored to a partial depth. Other options are possible as well.

Figure 6:
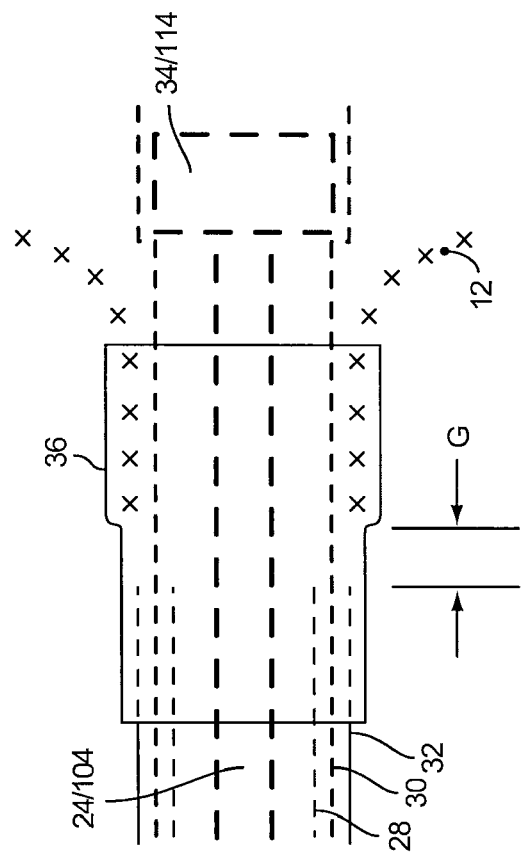
FIG. 6 is another delivery system detail illustration which concerns component spacing to ensure cover release from the implant.

FIG. 6 illustrates another detail relevant to consistent release performance in wedge-based variations of the subject invention. Namely, a gap "G" is advantageously provided between the proximal end of the implant and any jacket 32 and/or liner 28 that would interfere with wedge member 26 withdrawal past the end of the implant. Allowing the wedge to (at least partially) pass beyond the implant during actuation ensures that cover 36 opens to fully release the implant. The length of the gap will typically be between about 1 mm to about 2 mm to ensure desired action.

Also important is the amount of expansion that the wedge member(s) provide. Generally, expansion is at least about 0.004 inches but more typically about 0.006 to about 0.012 inches. While more expansion/interference may be desired in some cases, care should be taken not to introduce other system performance issues in maximizing the size of the wedge body (e.g., hindering crossing profile, mechanical advantage in addressing the cover or generating other interference issues).

[Note also, it may be desirable to introduce a chamfer or lead-in to the wedge to assist its introduction under the covered portion of the implant. However, no such feature has been observed as necessary when the components are sized appropriately. It may be preferred (at least in variations of the invention in which a single wedge body is employed) to minimize the wedge member length (e.g., size it to about 0.010 inches or less) to avoid significant effects on system flex performance. In any case, selecting and tuning the size, shape and performance of the constituent parts of the subject systems is within the knowledge of those with skill in the art.

Beyond such routine development considerations, the present invention includes additional exemplary architectures. Of these, delivery system 140 illustrated in FIG. 7 is essentially a one-sided variation of system 100 illustrated in FIGS. 3A-3C. More particularly, it uses a single wedge member 26 and expandable braid section 142 working together to effect cover release. The architecture also closely resembles that of delivery system 10 illustrated in FIG. 1A. However, core member 144 in the case of system 140 in FIG. 7 actually connects to the distal end of the braid. This connection can be made by soldering, welding, gluing, etc.

FIG. 8 shows another one-sided wedge-plus-braid expander type delivery system. In this configuration, delivery system 150 wedge member 152 is set distal to the braid expander section 154.

As another option (equally applicable to other systems as described herein), the expander section of braid need not comprise an extension of braid defining shaft 156. Rather, the shaft may comprise a hypotube sleeve 158 and liner 160, with the expander braid captured external thereto by an extension of cover 162 heat-shrink tube. Other attachment approach are possible as well.

The inclusion of coil 164 (e.g. comprising Stainless Steel or Nitinol ribbon) is also a notable feature. It serves as compressible buttresses to the expander braid layer to in generate a firm lock for the implant between the braid layer and cover.

In delivery system 150, the wedge 152 may comprise a solder joint attaching the core member to the braid. Alternatively, it may comprise a weld joint between the bodies and/or be supplemented with a band to help define a consistent geometry. In any case, the architecture of system 150 may offer advantages in action by first progressively expanding the cover with the braid and then "finish" by drawing the wedge under the implant to ensure the sheath opens for implant release.

In lieu of what one could call "belt-and-suspenders" approaches as taught in connection with FIGS. 7 and 8, the systems in FIGS. 9 and 10 rely only on braid-based expander members. Delivery system 170 illustrated in FIG. 9 is, in essence, a wedgeless version of system 140 illustrated in FIG. 7. As such, release action relies on braid expansion member 142 alone. Likewise, delivery system 180 as shown in FIG. 10 is analogous to delivery system 150 illustrated in FIG. 8, except that the braid and core member termination feature 182 is not sized to provide any wedging action to aid in cover release. In these systems, avoiding the "bump" otherwise present with a wedge member may help achieve more desirable crossing profiles. However, it may require heavier braid construction than embodiments that include one or more wedge features.

The final delivery system architecture illustrated here is shown in FIGS. 11A and 11B. The figures show delivery system 190 before and after implant deployment. In one sense, delivery system 190 operates like braid-expander systems 170 and 180 in that it uses changing angles of a compressed member to drive cover release. However, it is implemented with a compactable coil 192. Advantageously, the coil is isolated from moving across implant 12 by braid layer 32. In use, coil 192 is drawn down by core member 144 so its angle flattens to consequentially expand implant 10 and force cover 26 to open.

Apart from these various device architectures provided (in part) to enable the full generic scope of any of the appended claims, specific methods are still contemplated within the invention. An important application of the subject devices is presented in FIGS. 12A-12D.

Figure 12A:
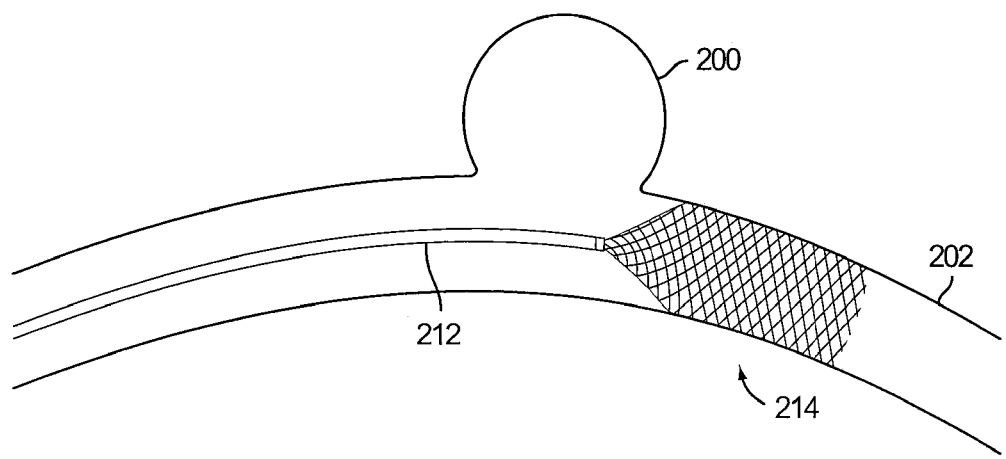
FIGS. 12A-D are side views depicting an exemplary embodiment of the implant delivery system at different stages of implant deployment in treating an aneurysm.
Figure 12B:
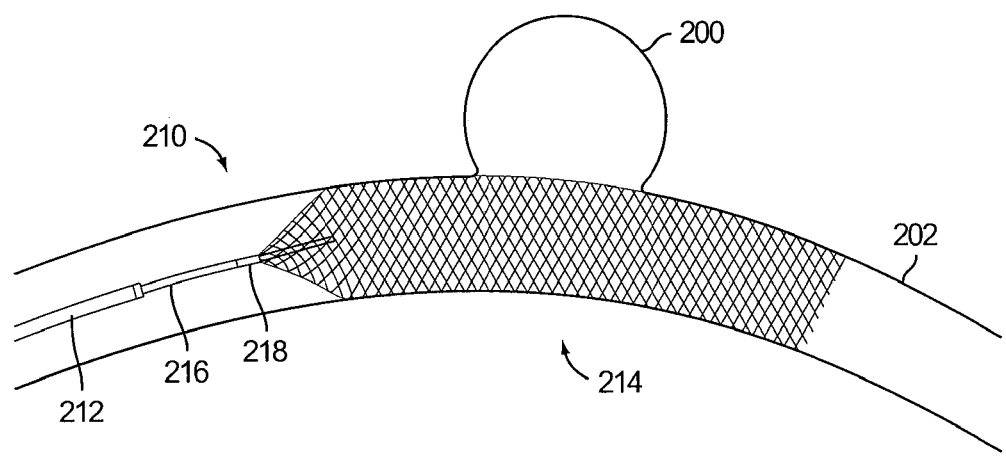
Figure 12C:
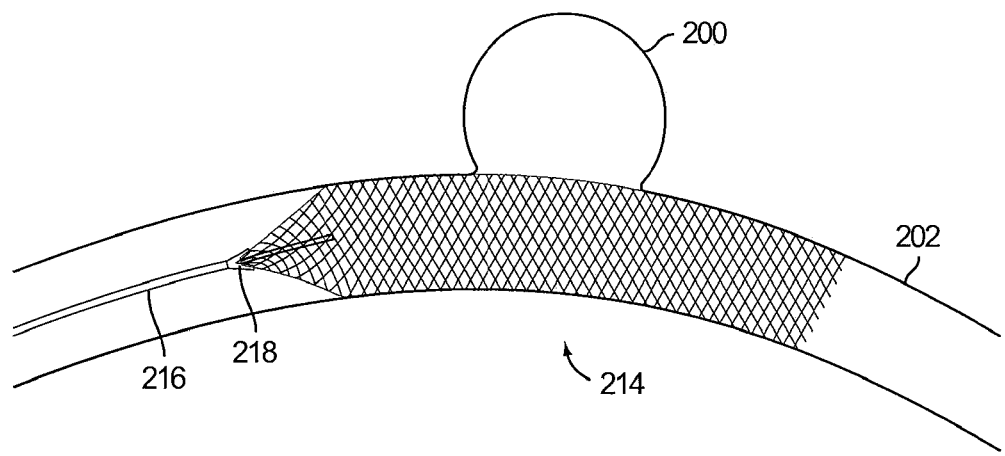
Figure 12D:
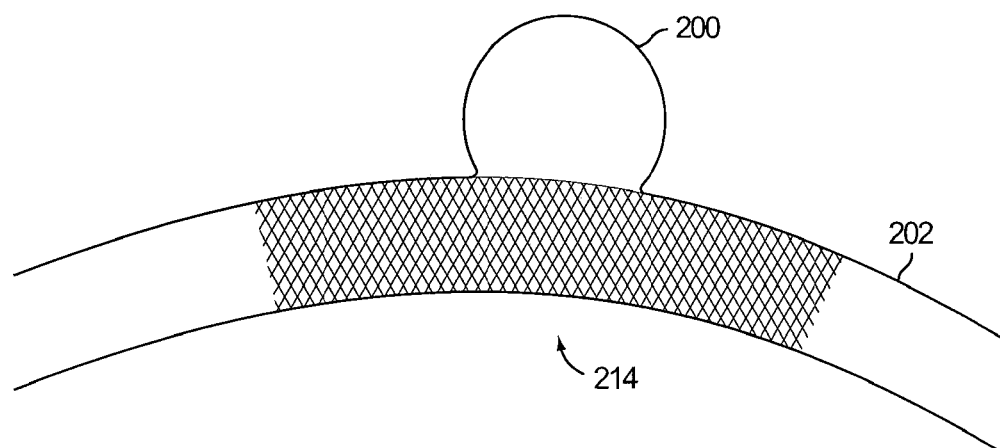

In these figures, pertinent implant deployment steps are illustrated in connection with treating a cerebral aneurysm. In this case, a sidewall aneurysm 200 has formed off of an artery 202. After removal from sterile packaging (not shown), and loading the delivery system 210 in a microcatheter 212 that has accessed a target site, the implant 214 is exposed as illustrated in FIG. 12A. To do so, the implant pusher (hidden in FIG. 12A) is typically held stationary, and the microcatheter withdrawn. Microcatheter withdrawal is continued until the entire implant 214 is exposed, attached to pusher 216 by cover 218 as shown in FIG. 12B. Then, the core member within the delivery system is withdrawn to rupture the cover as shown in FIG. 12C. After a quarter turn or straight withdrawal, the implant is free of the delivery system and implantation procedure complete as shown in FIG. 12D.

The subject methods may include each of the physician activities associated with implant positioning and release. As such, methodology implicit to the positioning and deployment of an implant device forms part of the invention. Such methodology may include navigating or tracking an implant through a catheter to a treatment site. In some methods, the various acts of implant introduction adjacent to an aneurysm considered. Other methods concern the manner in which the system is prepared for delivering an implant, for example attaching the implant to the delivery system. Any method herein may be carried out in any order of the recited events which is logically possible, as well as in the recited order of events, or slight modifications of those events or the event order.

Also, it is contemplated that any optional feature of the inventive variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language. Use of the term "invention" herein is not intended to limit the scope of the claims in any manner. Rather it should be recognized that the "invention" includes the many variations explicitly or implicitly described herein, including those variations that would be obvious to one of ordinary skill in the art upon reading the present specification. Further, it is not intended that any section of this specification (e.g., summary, detailed description, abstract, field of the invention) be accorded special significance in describing the invention relative to another or the claims. All references cited are incorporated by reference in their entirety. Although the foregoing invention has been described in detail for purposes of clarity of understanding, it is contemplated that certain modifications may be practiced within the scope of the appended claims.

The invention claimed is:

1. An implant delivery system comprising:
   an elongate sleeve having a lumen;
   an elongate core member slidably disposed within the sleeve lumen, the core member carrying one or more expanders thereon;

a braided implant disposed over the sleeve;

a proximal cover disposed over a proximal end of the implant such that a proximal end portion of the implant is radially constrained between the proximal cover and the sleeve; and a distal cover disposed over a distal end of the implant such that a distal end portion of the implant is radially constrained between the distal cover and the sleeve, wherein, in an engaged configuration, the one or more expanders are disposed distal to the proximal cover and proximal to the distal cover, and wherein the system is configured such that proximal withdrawal of the distal cover with respect to the proximal cover causes the one or more expanders to exert a radially outward force on the sleeve to open the proximal cover and the distal cover.

2. The system of claim 1, wherein withdrawing the distal cover with respect to the proximal cover places one or more of the expanders underneath the proximal end portion of the implant, thereby causing the proximal cover to open.

3. The system of claim 1, wherein the proximal cover is configured to open by tearing.

4. The system of claim 1, wherein the proximal cover is configured to open by rupturing.

5. The system of claim 1, wherein the one or more expanders comprises a wedge body.

6. The system of claim 1, wherein the one or more expanders comprises a coil.

7. The system of claim 1, wherein the sleeve comprises a tubular braid.

8. The system of claim 1, wherein the one or more expanders comprises a plurality of expanders carried by the core member.

9. An implant delivery system comprising:

an elongate core member carrying one or more expanders thereon;

a self-expanding implant disposed over the core member;

a proximal sheath disposed over and radially constraining a proximal end portion of the implant; and a distal sheath disposed over and radially constraining a distal end portion of the implant, wherein the system is configured such that bringing the proximal sheath and the distal sheath closer together urges the one or more expanders into a position underneath the proximal sheath and underneath the distal sheath, thereby rupturing the proximal sheath and the distal sheath, thereby releasing the proximal end portion of the implant and releasing the distal end portion of the implant.

10. The system of claim 9, further comprising a sleeve disposed radially between the core member and the implant.

11. The system of claim 10, wherein the sleeve is more radially expanded at a location that overlies the one or more expanders than over a location that does not overlie the one or more expanders.

12. The system of claim 10, wherein the core member and the one or more expanders are axially slidable with respect to the sleeve.

13. The system of claim 10, wherein the sleeve comprises a braid section.

14. The system of claim 9, wherein the one or more expanders comprises a wedge body.

15. The system of claim 9, wherein the one or more expanders comprises a coil.

16. A method of implant delivery comprising:

advancing a delivery system to an intravascular target site, the delivery system comprising a core member, an implant mounted over a distal portion of the core member, one or more expanders underlying the implant, a proximal cover overlying a proximal end portion of the implant, and a distal cover overlying a distal end portion of the implant;

proximally retracting the distal cover with respect to the proximal cover, thereby radially expanding an intermediate portion of the implant; and further proximally retracting the distal cover with respect to the proximal cover such that the one or more expanders at least partially underlies the proximal cover and at least partially underlies the distal cover, thereby applying an expansive force to open the proximal cover and the distal cover to release the implant.

17. The method of claim 16, wherein proximally retracting the distal cover comprises rupturing and/or tearing the proximal cover and the distal cover.

18. The method of claim 16, wherein the one or more expanders comprises a wedge body, and wherein proximal retraction of the distal cover brings the wedge body into engagement with the implant.

19. The method of claim 16, wherein the one or more expanders comprises a coil, and wherein proximal retraction of the distal cover brings the coil into engagement with the implant.

20. The method of claim 16, wherein the delivery system further comprises a sleeve disposed radially between the implant and the one or more expanders, and wherein proximally retracting the distal cover with respect to the proximal cover comprises retracting the one or more expanders with respect to the sleeve such that the one or more expanders underlies both the sleeve and the proximal cover.

* * * * *